US 6,672,871 B2

(12) United States Patent
Hurson

(10) Patent No.: US 6,672,871 B2
(45) Date of Patent: Jan. 6, 2004

(54) COPING WITH STANDOFFS

(75) Inventor: Steven M. Hurson, Yorba Linda, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/881,860

(22) Filed: Jun. 15, 2001

(65) Prior Publication Data
US 2002/0028425 A1 Mar. 7, 2002

Related U.S. Application Data
(60) Provisional application No. 60/212,256, filed on Jun. 19, 2000.

(51) Int. Cl.7 .......................... A61C 13/225; A61C 8/00
(52) U.S. Cl. ...................... 433/172; 433/173; 433/180
(58) Field of Search ............................... 433/172, 173, 433/174, 175, 176, 180, 181, 182, 183; 264/19

(56) References Cited

U.S. PATENT DOCUMENTS

| 2,799,933 A | * | 7/1957 | Newstadter ............... 433/183 |
| 3,224,050 A | | 12/1965 | Redtenbacher ............. 164/34 |
| 3,742,605 A | | 7/1973 | Cooper .................... 433/40 |
| 4,227,877 A | | 10/1980 | Tureaud et al. ............ 433/37 |
| 4,416,629 A | * | 11/1983 | Mozsary et al. ........... 433/174 |
| 4,447,210 A | | 5/1984 | Hidaka et al. ............. 433/173 |
| 4,483,675 A | | 11/1984 | Marshall .................. 433/141 |
| 4,575,340 A | * | 3/1986 | Lustig ..................... 433/173 |
| 4,955,811 A | | 9/1990 | Lazzara et al. ............ 433/173 |
| 5,049,073 A | | 9/1991 | Lauks ..................... 433/173 |
| 5,073,111 A | | 12/1991 | Daftary ................... 433/173 |
| 5,145,371 A | | 9/1992 | Jorneus ................... 433/173 |
| 5,213,498 A | | 5/1993 | Pelerin .................... 433/37 |
| 5,613,854 A | | 3/1997 | Sweatt .................... 433/223 |
| 5,667,384 A | | 9/1997 | Sutter et al. .............. 433/172 |
| 5,685,715 A | | 11/1997 | Beaty et al. .............. 433/173 |
| 5,688,123 A | | 11/1997 | Meiers et al. ............. 433/173 |
| 5,704,788 A | * | 1/1998 | Milne ..................... 433/173 |
| 5,829,981 A | | 11/1998 | Ziegler ................... 433/214 |
| 5,904,483 A | | 5/1999 | Wade ..................... 433/173 |

FOREIGN PATENT DOCUMENTS

| CH | 196072 | 5/1938 |
| DE | 31 10 694 A1 | 3/1981 |
| DE | 40 15 008 A1 | 5/1990 |
| GB | 470444 | 8/1937 |

OTHER PUBLICATIONS

Strauman Dental. "Crown and bridge restorations on ITI solid abutments." May 1999. 21 pages.

* cited by examiner

Primary Examiner—John J. Wilson
(74) Attorney, Agent, or Firm—Knobbe, Martens, Olson & Bear, LLP

(57) ABSTRACT

A prosthodontic assembly comprises a restoration having a cavity defined by a first surface and an abutment positioned within the cavity. The assembly further comprises a plurality of standoffs positioned in between the first surface and the abutment to provide a gap. Methods for forming the restoration are also disclosed.

46 Claims, 21 Drawing Sheets

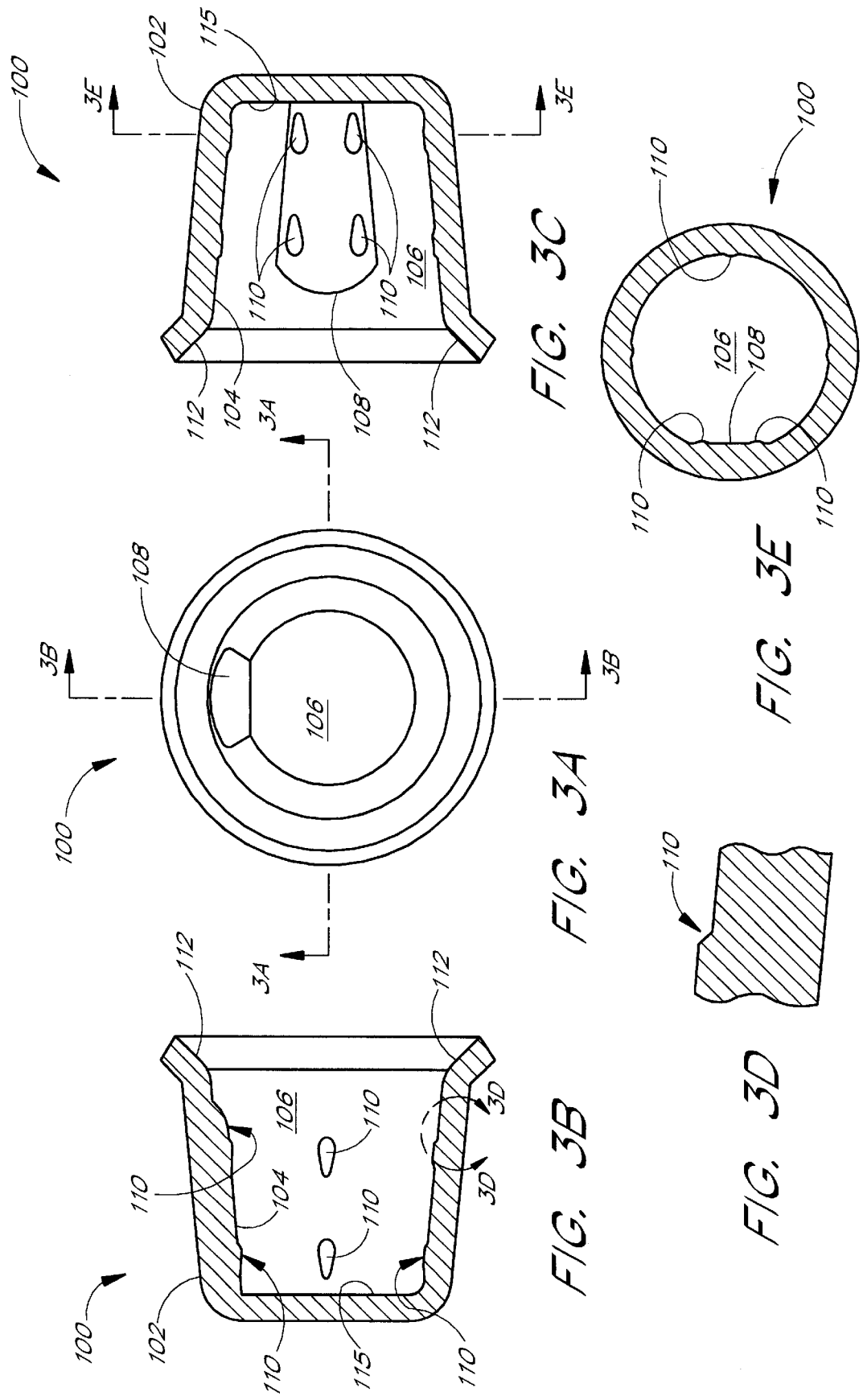

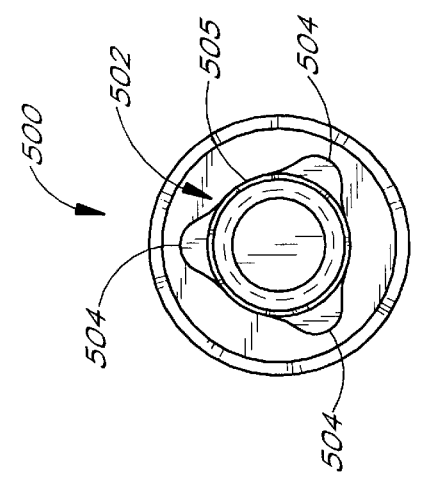
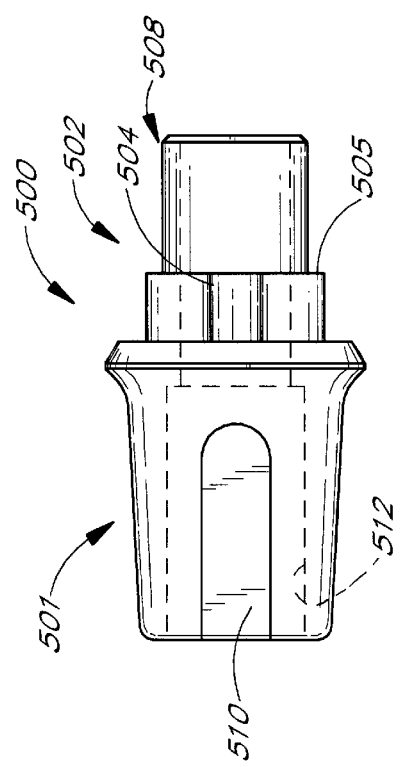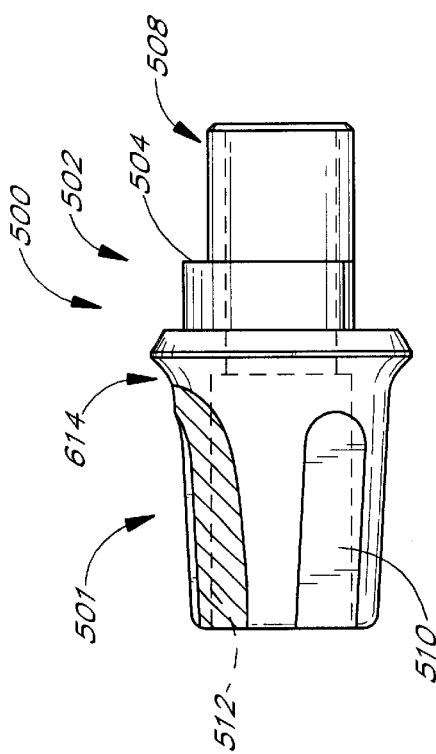
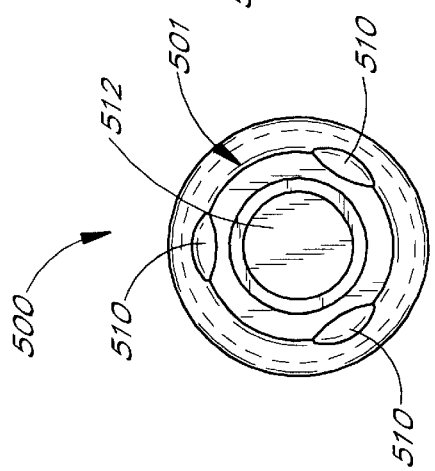

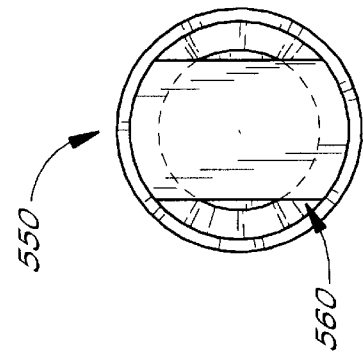
FIG. 9D
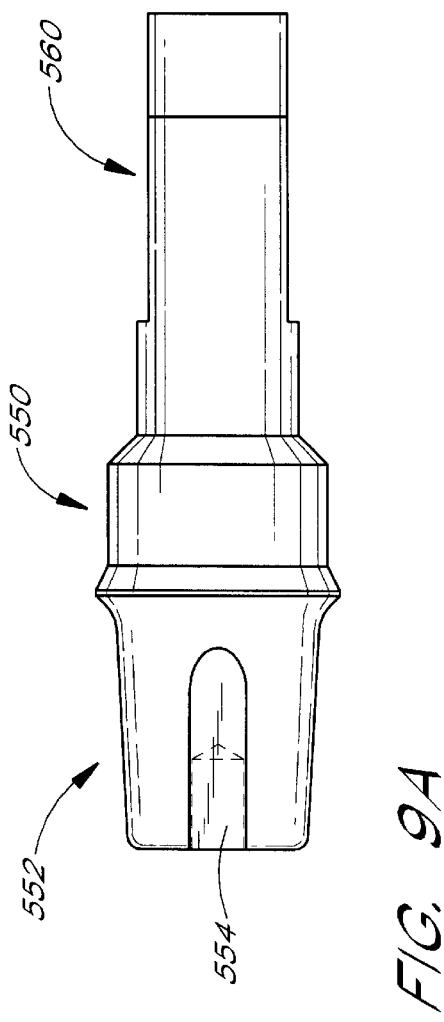
FIG. 9A
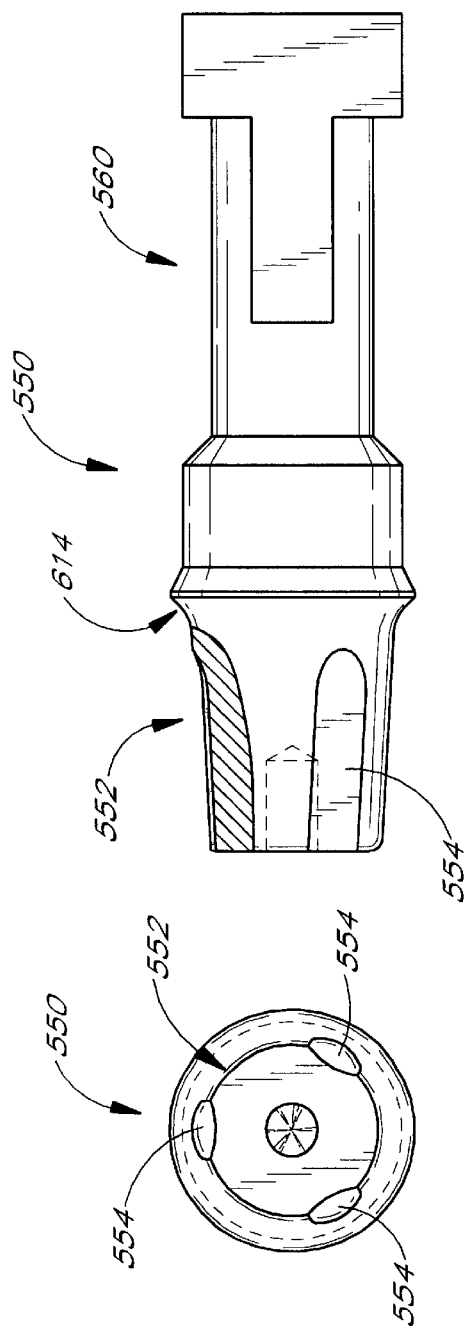
FIG. 9B
FIG. 9C

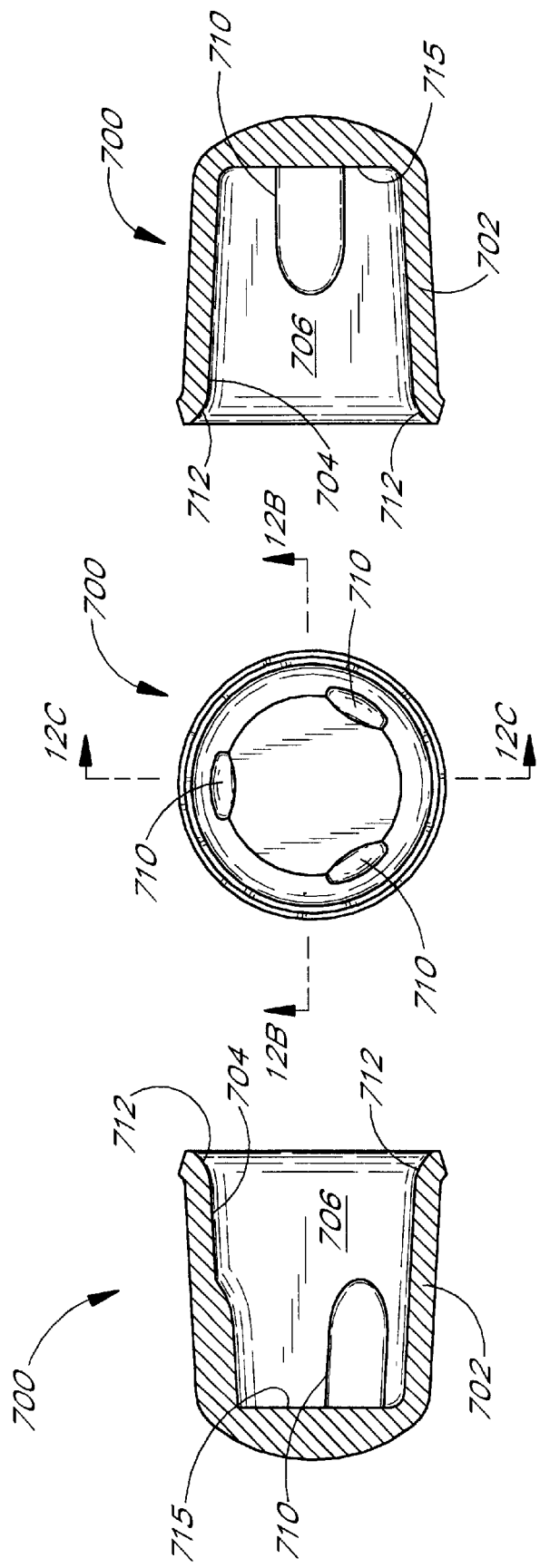

COPING WITH STANDOFFS

CROSS REFERENCE TO RELATED APPLICATION

The present application claims priority and benefit under 35 U.S.C. §119(e) of U.S. Provisional Patent Application Ser. No. 60/212,256 filed Jun. 19, 2000, the entire contents of which are expressly incorporated herein.

BACKGROUND OF THE INVENTION

1. Field of the Invention

The present invention relates generally to dental restorations and, more particularly, to a coping that is used to form a dental prosthesis.

2. Description of the Related Art and Summary of the Invention

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant to be implanted. Then, the dental implant is inserted into the hole in the jawbone, typically by screwing, although other techniques are known for introducing the implant in the jawbone.

After the implant is initially installed in the jawbone, a temporary healing cap can be secured over the exposed proximal end in order to seal an internal bore of the implant. The patient's gums are then sutured over the implant to allow the implant site to heal and to allow the desired osseointegration to occur. Complete osseointegration typically takes anywhere from four to ten months.

During Stage II, the surgeon reaccesses the implant fixture by making an incision through the patient's gum tissues. The healing cap is then removed, exposing the proximal end of the implant. The interior of the implant is thoroughly cleaned and dried. The surgeon can then attach a final abutment to the implant. To accurately record the position, the orientation and the shape of the final abutment within the mouth, the surgeon takes a mold or impression of the patient's mouth. Stage II is typically completed by securing a protective cap to the abutment with temporary cement. Alternatively, a conventional temporary restoration can be attached to the abutment.

Stage III involves fabricating and placement of a final restoration to the implant fixture. A laboratory technician makes the stone plaster model of the patient's mouth from the impression that was taken in Stage II. To create the model, the technician typically repositions an analogue of the final abutment into the impression. The technician then pours plaster into the impression to create a hard stone plaster model of the patient's mouth. Based on this model, the technician constructs a final restoration. The final restoration typically includes an internal cavity that is configured to fit over the final abutment. Typically, the final step in the restorative process is securing the final restoration to the final abutment with cement.

To ensure that there is adequate space for the cement, the internal cavity of the final restoration generally is slightly larger than the final abutment. To create the slightly larger internal cavity, the technician typically paints a die spacer onto the analogue. The die spacer typically has a thickness of approximately 25 to 50 microns. The analogue is then covered with wax. The wax can then be used in an investment casting process to create a metal coping. The spacer die ensures that the internal cavity of the metal coping has an internal cavity that is 25 to 50 microns larger than the final abutment. To form the prosthesis, the metal coping is typically covered with a tooth-like material, such as, for example, porcelain.

SUMMARY OF THE INVENTION

Because the internal cavity of the coping is 25 to 50 microns larger than the final abutment, a gap exists between the coping and the final abutment. This gap provides room for the cement. Without this gap, the prosthesis would not sit all the way down upon the final abutment due to the added thickness of the cement. Moreover, the size of the gap is important for achieving the desired cement thickness between the prosthesis and the final abutment. If the gap is too large, the cement thickness becomes too thick and the integrity of the cement is impaired. If the gap is too small, the cement thickness becomes too thin and the cement will have poor resistance to shear stresses. Also, the variability of the thickness of the spacer die and the pressure applied by the dentist during the cementing process can cause the final restoration to sit unevenly upon the final abutment and/or sit too low or high. Thus, there is a need for a more predictable method of forming the required gap between the coping and the final abutment.

Accordingly, one aspect of the present invention is a final restoration for a prosthodontic assembly. The restoration comprises a body portion having a proximal end, a distal end and an inner surface that defines an internal cavity and at least one standoff that extends from the inner surface towards a center of the internal cavity.

Another aspect of the present invention is a coping for creating a final restoration. The coping comprises a body portion having a proximal end, a distal end and an inner surface that defines an internal cavity and at least one standoff that extends from the inner surface towards a center of the internal cavity.

Yet another aspect of the present invention is a method for creating a final restoration. A coping is provided. The coping has a body portion that includes a proximal end, a distal end and an inner surface that defines an internal cavity and at least one standoff that extends from the inner surface towards a center of the internal cavity. An analogue of a final abutment is also provided. The analogue and the final abutment each have an upper region configured to fit within the internal cavity of the coping. The coping is placed over the upper region of the analogue. A material suitable for investment casting is applied to an outer surface of the coping. The coping and the material suitable for investment casting are encased in an investment material. The coping and the material suitable for investment casting are melted. The coping and the material suitable for investment casting are removed from the investment material and a cavity within the investment material is filled with a material suitable for forming a part of a final restoration.

Another aspect of the present invention is a method for creating a final restoration. A coping is provided. The coping has a body portion made of a material suitable for forming a final restoration. The body portion comprises a proximal end, a distal end and an inner surface that defines an internal cavity and at least one standoff that extends from the inner surface towards a center of the internal cavity. A toothlike material is attached to the coping to form a final restoration. The final restoration is attached to a final abutment.

Still yet another aspect of the present invention is a method for forming a final restoration. A transfer coping is provided. The transfer coping has a body portion comprising a proximal end, a distal end and an inner surface that defines an internal cavity, a flanged region, and at least one standoff that extends from the inner surface towards a center of the internal cavity. The transfer coping is placed over an upper region of a final abutment that is secured to a dental implant within a patient's mouth. An impression of the patient's mouth is formed by placing impression material around the transfer coping and the final abutment. The impression and the transfer coping are removed from the patient's mouth. Model material is poured into the impression to form a model of the patient's mouth and the upper region of the final abutment.

Another aspect of the present invention is a final restoration for a prosthodontic assembly. The restoration comprises a body portion having a proximal end, a distal end and an inner surface that defines an internal cavity. The inner surface including a top region, a flanged region. The restoration further comprising at least one standoff that extends from the inner surface towards a center of the internal cavity. The at least one standoff and the flanged region configured to produce a substantially uniform gap between the final restoration and a final abutment upon which the final restoration rests.

Another aspect of the present invention is a coping. The coping comprises a body portion having a proximal end, a distal end and an inner surface that defines an internal cavity. The inner surface includes a top region and a flanged region. The coping further comprising and at least one standoff that extends from the inner surface towards a center of the internal cavity. The at least one standoff and the flanged region configured to produce a substantially uniform gap between the final restoration and a final abutment upon which the final restoration rests.

Another aspect of the present invention is a prosthodontic assembly. The assembly comprises a restoration having a cavity defined by a first surface and an abutment positioned within the cavity. The assembly further comprises a plurality of standoffs positioned in between the first surface and the abutment to provide a gap.

Another aspect of the present invention is a prosthodontic assembly comprising a first prosthodontic and a coping. The first prosthodontic component comprises an upper region with at least one recess. The coping is configured for creating a final restoration. The coping comprises a body portion having a proximal end, a distal end and an inner surface that defines an internal cavity and at least one standoff that extends from the inner surface towards a center of the internal cavity. The at least one standoff is configured to fit within the at least one recesses so as to prevent relative rotation between the first prosthodontic component and the coping. The at least one standoff is also configured to provide a gap between the inner surface of the coping and the upper region of the first prosthodontic component.

For purposes of summarizing the invention and the advantages achieved over the prior art, certain objects and advantages of the invention have been described above herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of the invention will now be described with reference to the drawings of the preferred embodiments, which are intended to illustrate and not to limit the invention, and in which:

FIG. 3A is a bottom plan view of a coping having certain features and advantages according to the present invention.

FIG. 3B is a cross-sectional view taken along line B—B of FIG. 3A.

FIG. 3C is a cross-sectional view taken along line C—C of FIG. 3A.

FIG. 3D is a close-up view of detail D of FIG. 3B.

FIG. 3E is a cross-sectional view taken though line 3E-3E of FIG. 3C.

FIG. 8A is a side view of a final abutment having certain features and advantages according to the present invention.

FIG. 8B is another side view the final abutment rotated 90 degrees from the view shown in FIG. 8A.

FIG. 8C is top plan view of the final abutment of FIG. 8A.

FIG. 8D is a bottom plan view of the final abutment of FIG. 8A.

FIG. 9A is a side view of an analogue having certain features and advantages according to the present invention.

FIG. 9B is another side view the analogue rotated 90 degrees from the view shown in FIG. 9A.

FIG. 9C is top plan view of the analogue of FIG. 9A.

FIG. 9D is a bottom plan view of the analogue of FIG. 9A.

FIG. 12A is a bottom plan view of another modified coping having certain features and advantages according to the present invention.

FIG. 12B is a cross-sectional view taken along line B—B of FIG. 10A.

FIG. 12C is a cross-sectional view taken along line C—C of FIG. 10A.

DETAILED DESCRIPTION OF THE PREFERRED EMBODIMENT

Figure 1A:
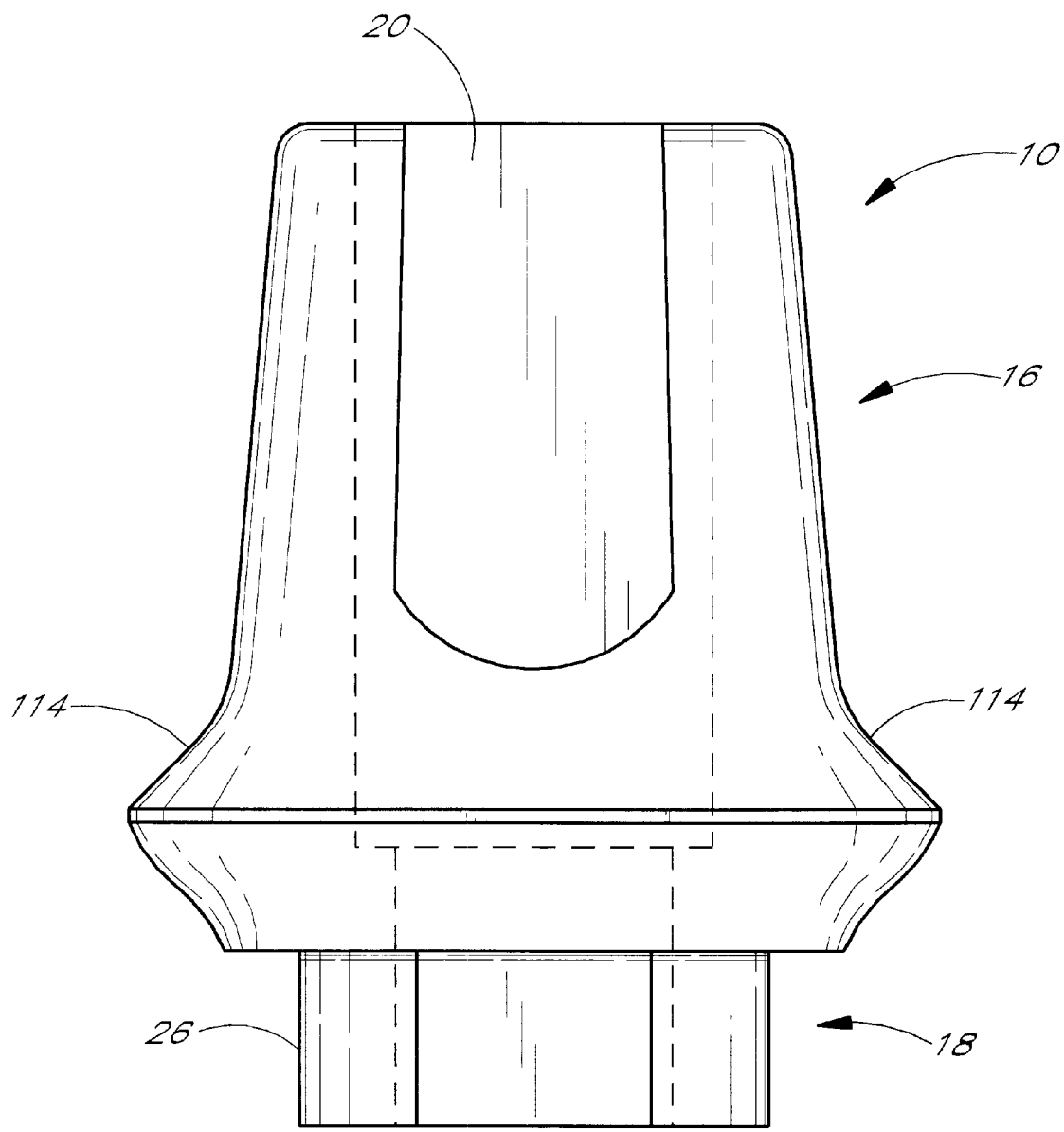
FIG. 1A is a side view of an exemplary final abutment.
Figure 1B:
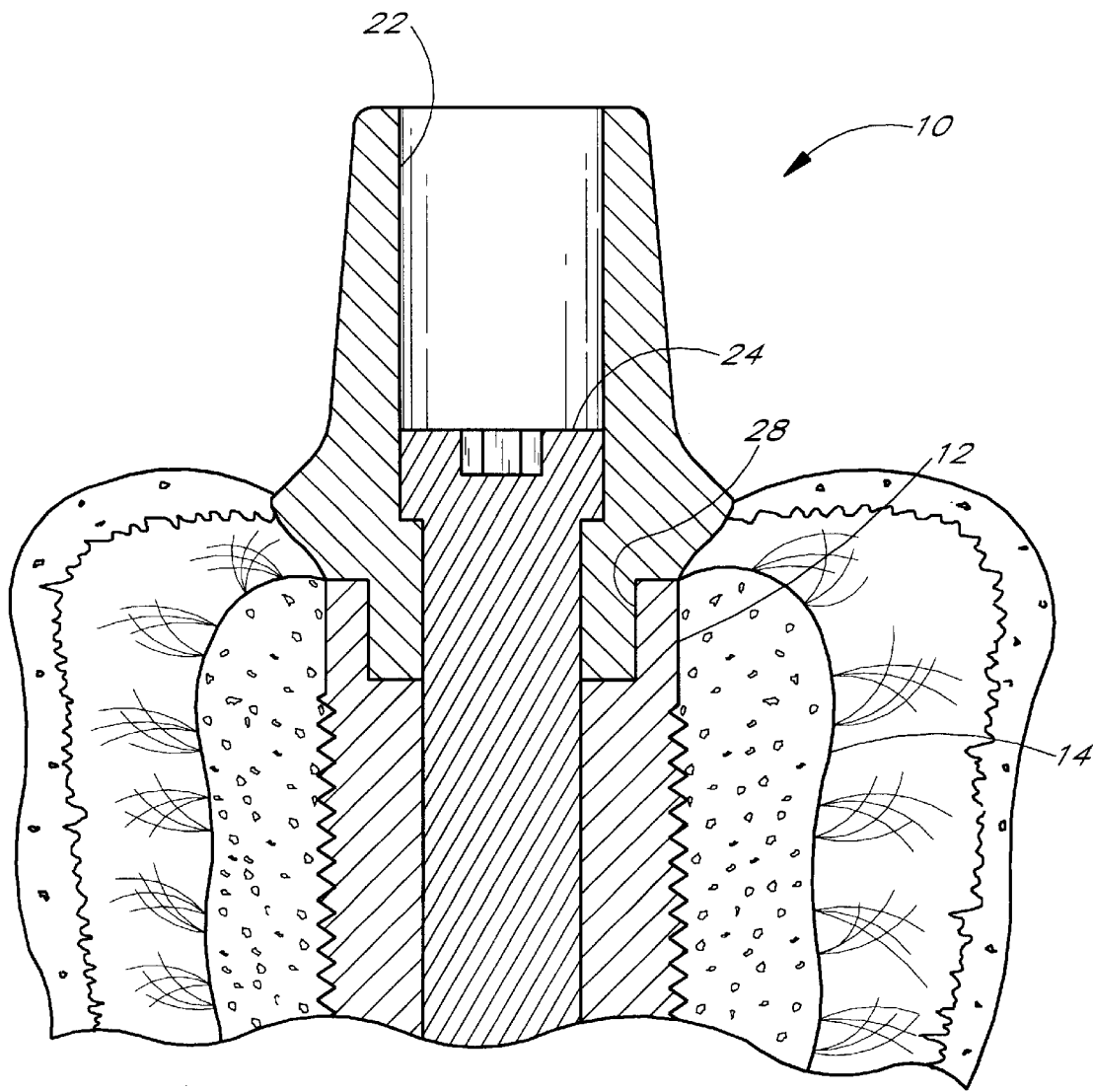
FIG. 1B is a cross-sectional side view of the exemplary final abutment of FIG. 1B, attached to an exemplary dental implant.

FIGS. 1A and 1B illustrate an exemplary final abutment 10 and part of an exemplary dental implant 12 (see FIG. 1B). The final abutment 10 and the dental implant 12 may comprise any of a number of conventional structures, which well known in the art. Accordingly, where any component of the final abutment 10 or implant 12 has not been illustrated or described in detail, reference may be had to conventional or known structures.

As shown in FIG. 1B, the dental implant 12 is inserted into the patient's jawbone 14. The final abutment 10 is configured to mate with the dental implant 12 and to support other dental components such as a final restoration. Accordingly, as best seen in FIG. 1A, the final abutment 10 includes an upper region 16 and an anti-rotation device 18. The upper region 16 includes one or more anti-rotation features 20. In the illustrated final abutment 10, the anti-rotation feature comprises a groove or recess 20 formed on the outer surface of the upper region 16. The recess 20 helps to orient and prevent the rotation of a final restoration, which will be eventually placed on top of the final abutment 10. The final restoration, therefore, has an inner surface that is configured to match the shape of the upper region 16 of the final abutment 10. Of course, those skilled in the art will readily appreciate that the upper region 16 can have a variety of other shapes giving due consideration to the goal of providing an anti-rotational interface between the final restoration and the final abutment 10. In some arrangements, the final abutment 10 may be formed without the anti-rotation component.

As best seen in FIG. 1B, the illustrated final abutment 10 includes an inner bore 22. The inner bore 22 is configured to receive a coupling screw 24, which is used to secure the final abutment 10 to the dental implant 12 as seen in FIG. 1B. Of course, those of skill in the art will understand that in some arrangements the final abutment 10 can be formed without the inner bore 22. In such arrangements, the final abutment 10 can include a threaded post that is configured to directly engage the implant 12.

With reference to FIGS. 1A and 1B, the anti-rotational device 18 of the illustrated final abutment 10 comprises a hexagonal protrusion 26 that is configured to fit within an anti-rotation portion 28 of the implant 12. In the illustrated arrangement, the anti-rotation portion 28 comprises a hexagonal recess. Of course, those of skill in the art will recognize that the anti-rotational device 18 and the anti-rotation portion 28 of the implant 12 can be formed in a variety of other ways giving due consideration to the goal of preventing relative rotation between the final abutment 10 and the implant 12. For example, the final abutment 10 could include a hexagonal recess that is configured to receive a hexagonal protrusion situated on the top surface of the implant 10. Alternative complementary surface structures may also be used such as other polygonal or non-round configurations, splines or other structures known in the art. Moreover, the final abutment 10 and the implant 12 can be formed without an anti-rotational means 18 or an anti-rotation portion 28. For example, the final abutment 10 can include a threaded post that is configured to engage the implant 12 directly.

Figure 2A:
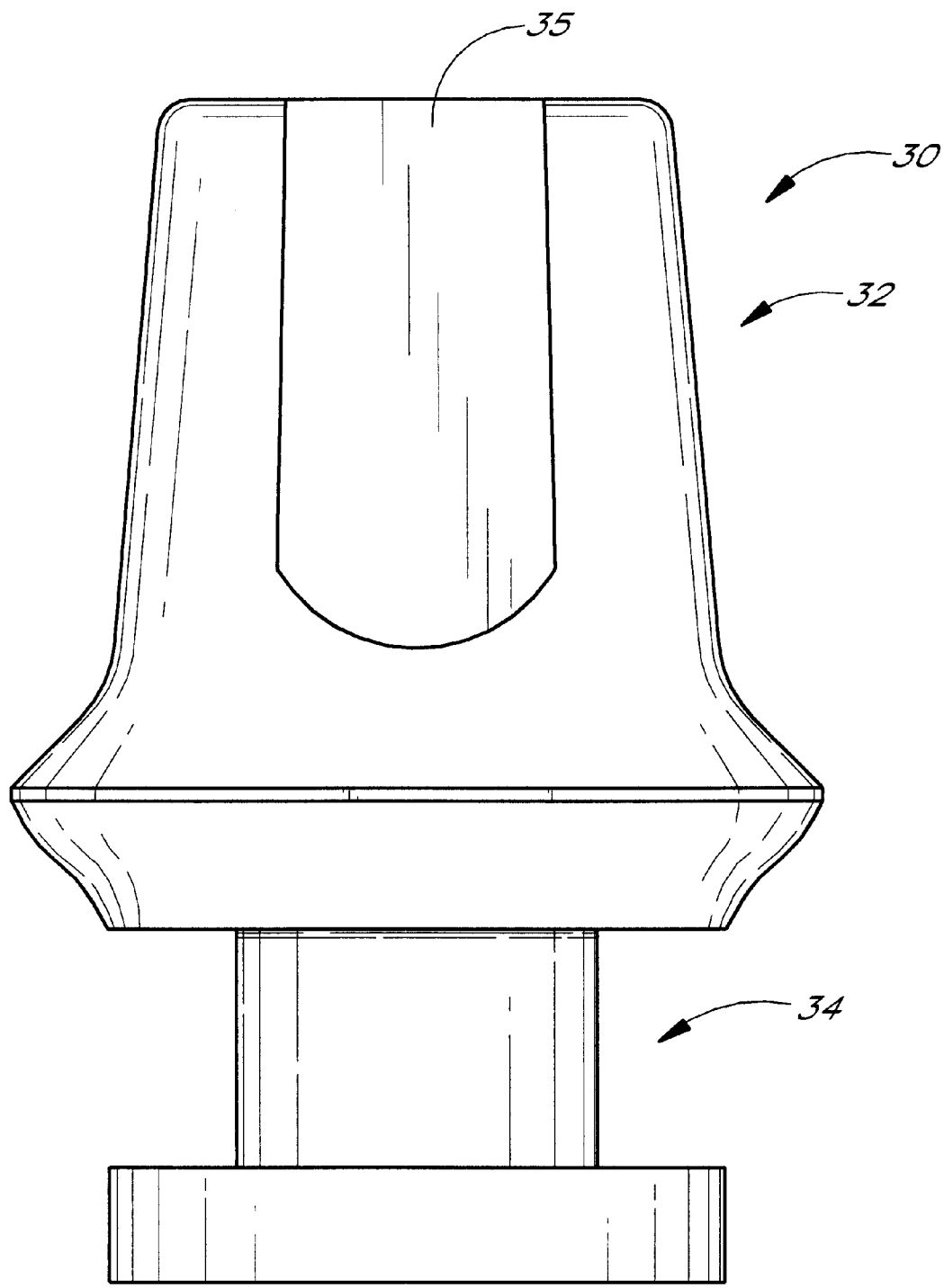
FIG. 2A is a side view of an exemplary analogue of the final abutment of FIG. 1.
Figure 2B:
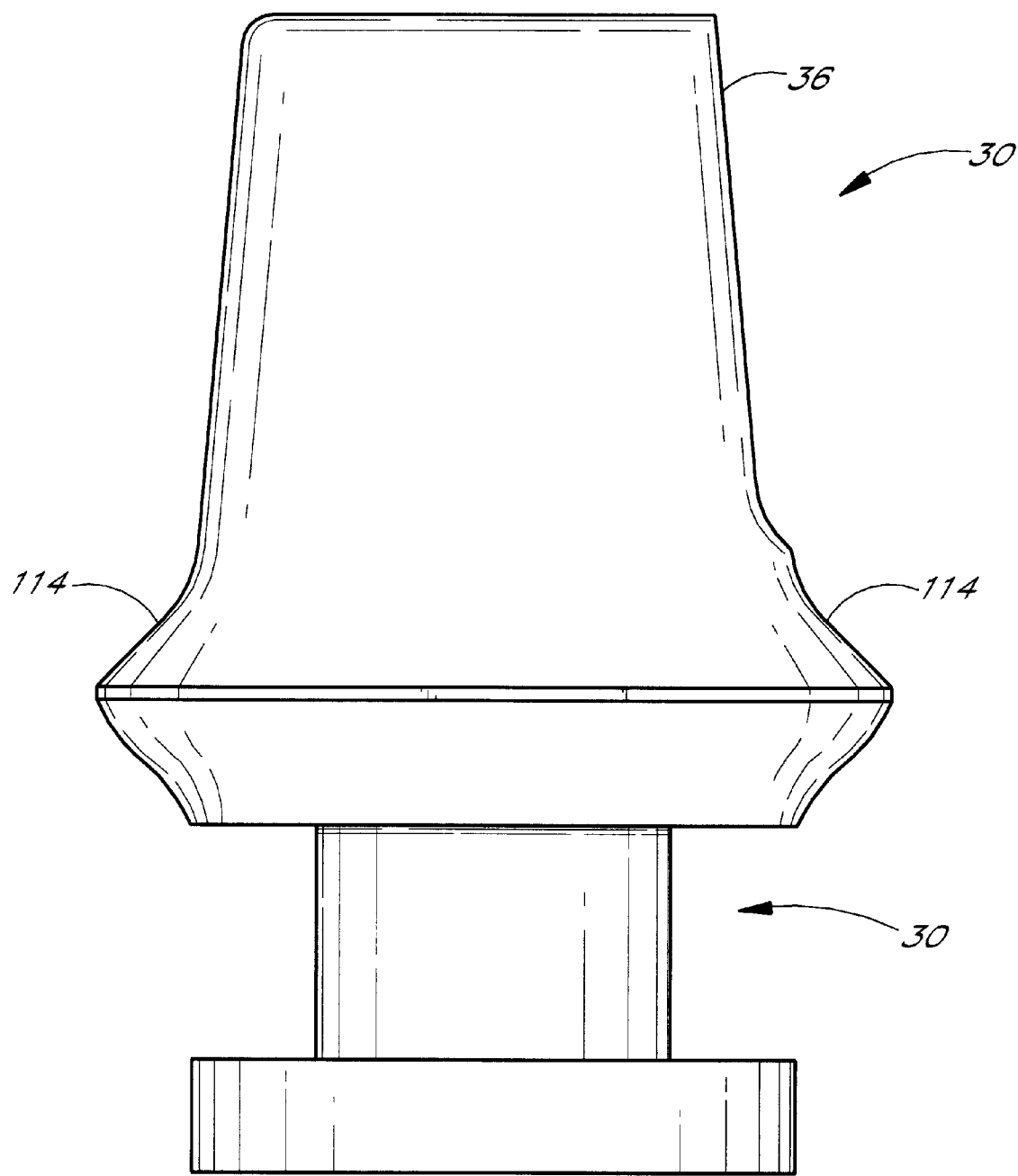
FIG. 2B is another side view the exemplary analogue rotated 90 degrees from the view shown in FIG. 2A.

FIGS. 2A and 2B illustrate an exemplary analogue 30 for the final abutment 10 described above. The analogue 30 includes an upper region 32 that has substantially the same shape and size as the upper region 16 of the final abutment 10. Accordingly, the upper region 32 of the illustrated analogue 30 also includes a groove or recess 36. The analogue 30 also includes a lower region 34, which, as will be explained below, is configured to be retained within, by way of example, a stone plaster model of the patient's mouth.

Figure 2C:
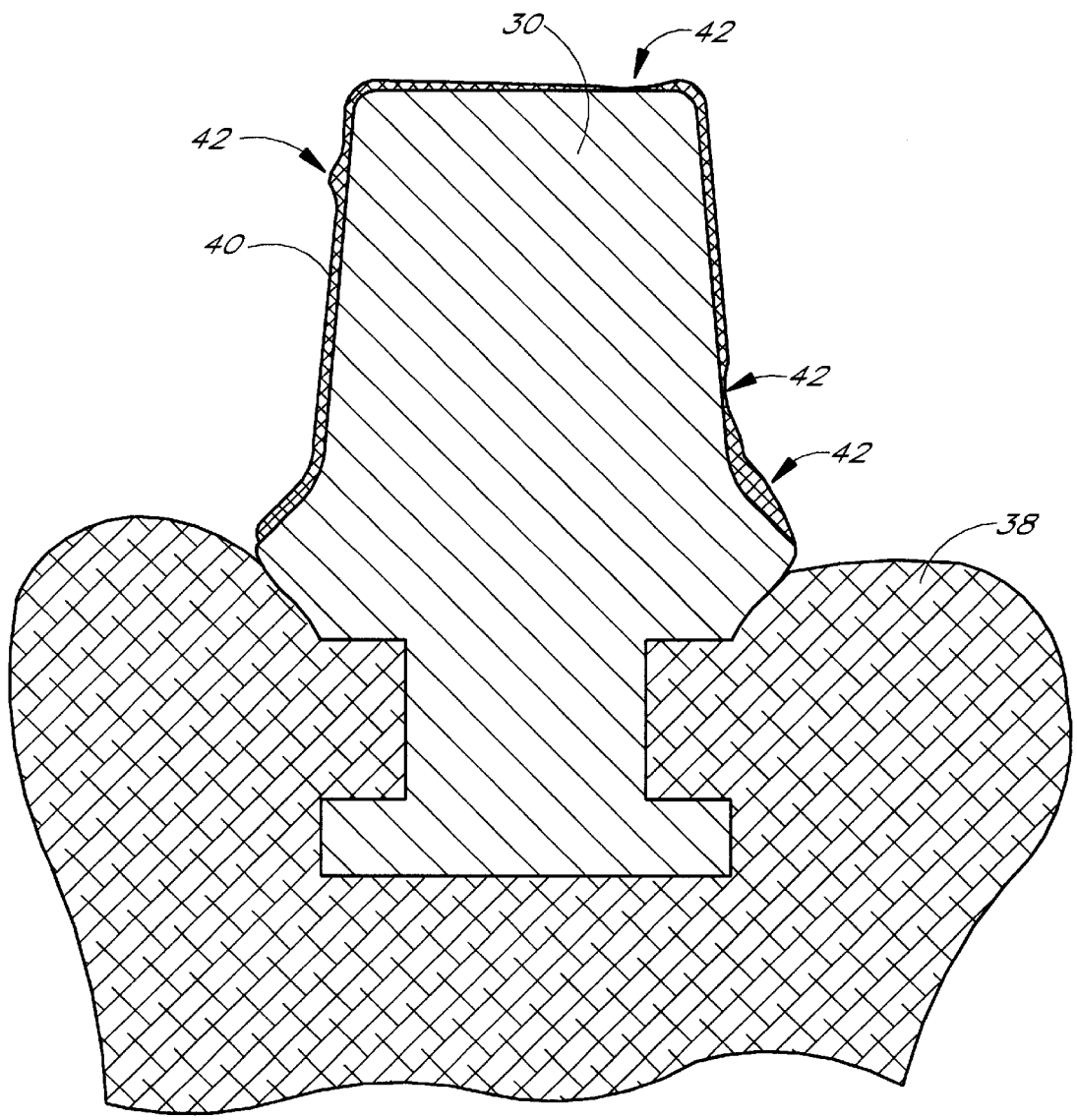
FIG. 2C is a cross-sectional side view of the exemplary analogue of FIG. 2A embedded in a plaster model.

As mentioned above, the surgeon takes an impression of the patient's mouth to accurately record the position, the orientation and the shape of the final abutment 10 within the patient's mouth. A technician then positions the analogue 30 into the impression and pours plaster into the impression to create a hard stone plaster model 38 of the patient's mouth, as shown in FIG. 2C. Of course, in modified arrangements, a stone plaster model of the patient mouth can be made in several other ways. For example, a transfer pin (not shown) or transfer cap (not shown) can be used to create a model that accurately records the position, shape and orientation of the dental implant 10 within the patient's mouth. In such an arrangement, the transfer pin or transfer cap is coupled to the dental implant. An impression is then taken of the patient's mouth. Once the impression is taken, a technician attaches an analogue of the dental implant to the transfer pin or transfer cap, which either remained embedded in the impression material (transfer cap) or was repositioned in the impression by a technician (transfer pin). Plaster is then poured into the impression to create a stone plaster model of the patient's mouth. An analogue of the final abutment is then attached to the analogue of the dental implant.

As shown in FIG. 2C, die spacer 40 typically is applied to the upper region 32 of the analogue 30. After the die spacer 40 dries, the die spacer 40 typically has a thickness t of approximately twenty to fifty microns. However, it is generally difficult to control the thickness of the die spacer 40 and the die spacer 40 is often applied unevenly. Accordingly, there are discontinuities 42 at which the die spacer 40 is thicker and/or thinner than optimally desired.

Figure 2D:
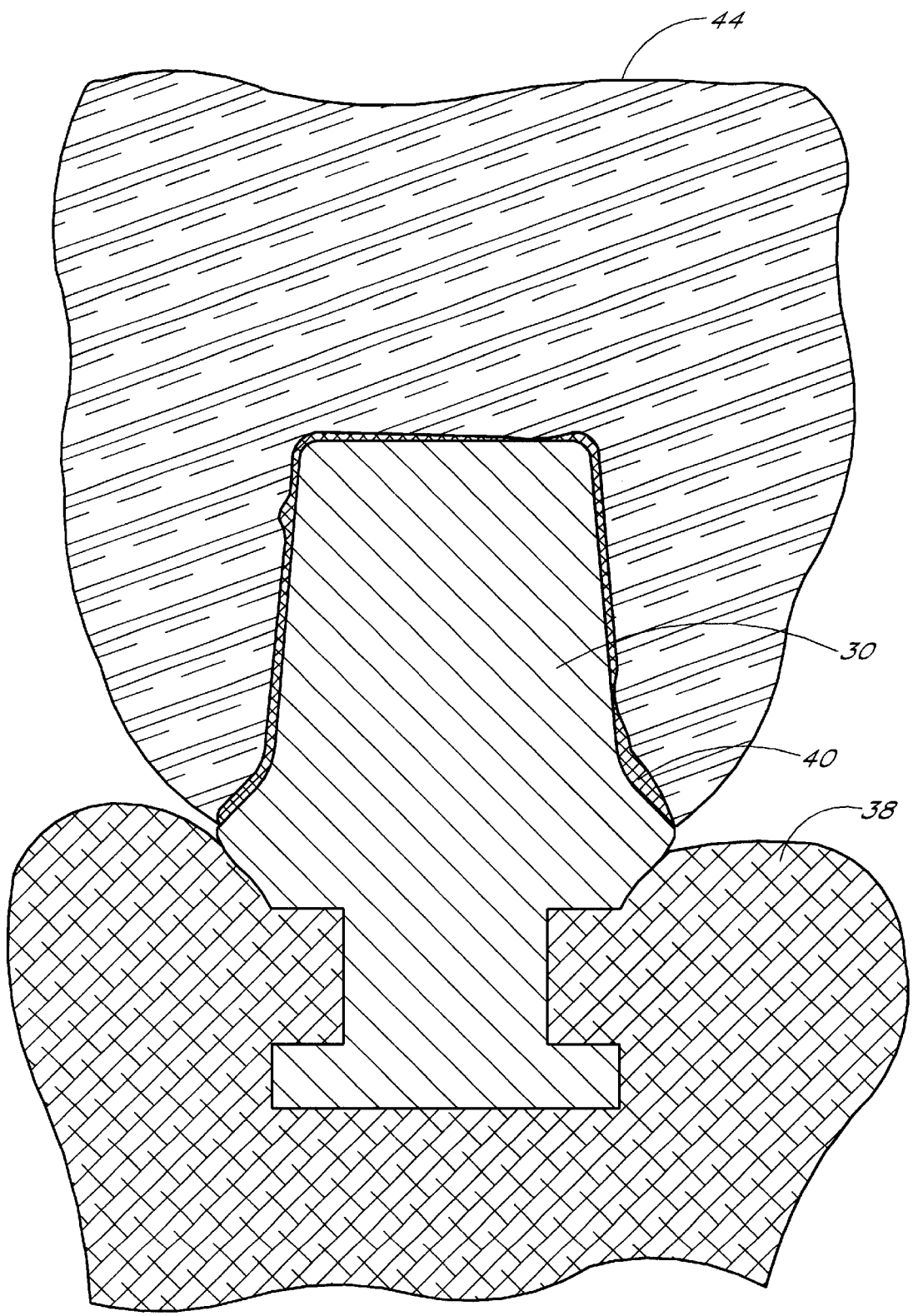
FIG. 2D is a cross-sectional side view of the exemplary analogue of FIG. 2A covered with a wax model of a metal coping.
Figure 2E:
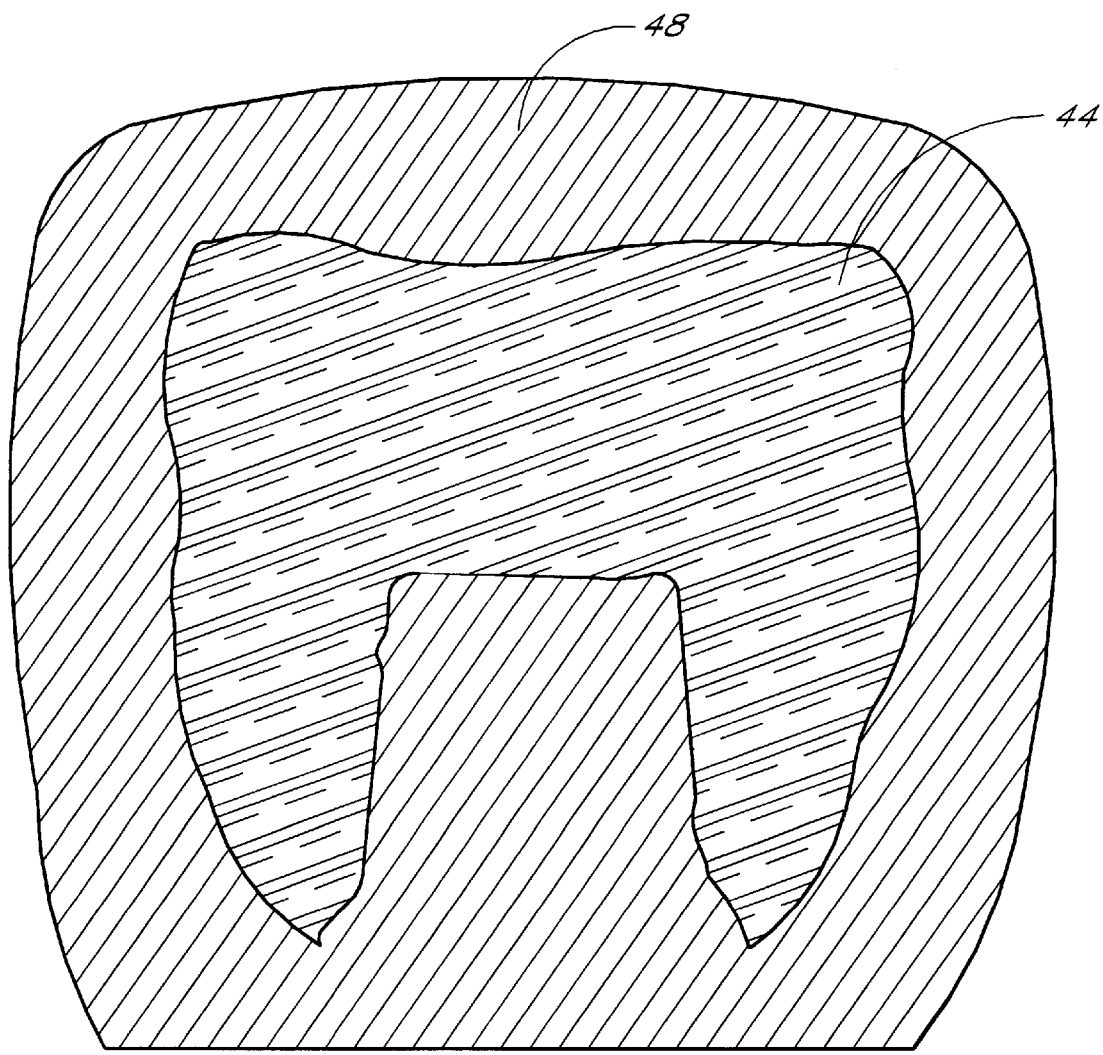
FIG. 2E is a cross-sectional side view of an investment casting of the wax model of FIG. 2D.
Figure 2F:
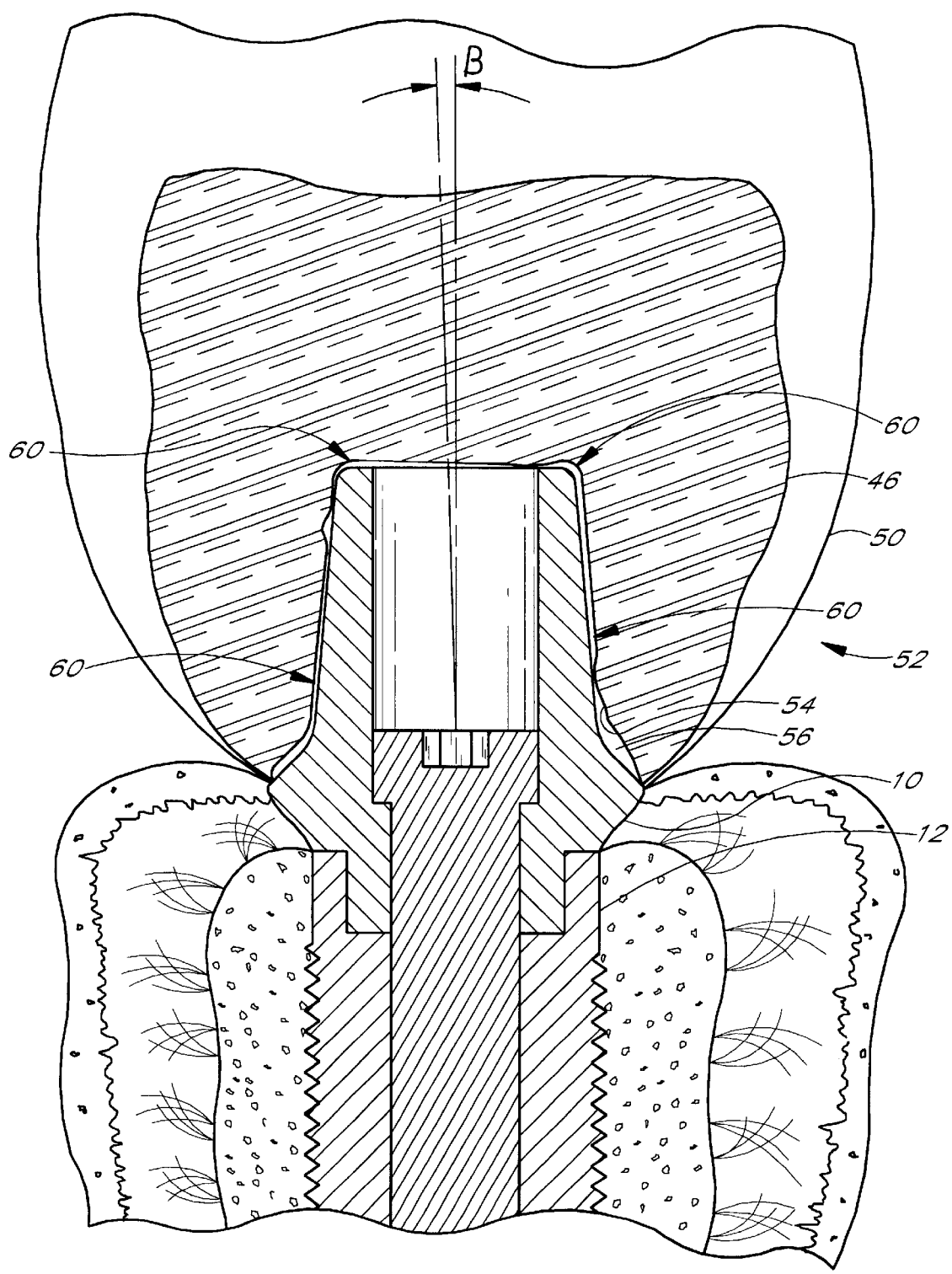
FIG. 2F is a cross-sectional side view of a final restoration attached to the final abutment of FIG. 1B.

As shown in FIG. 2D, after the die spacer 40 dries, the analogue 30 is typically covered with wax 43 or similar material to form model 44. The model 44 can be used to create a metal coping by covering the model 44 with investment material 48 as shown in FIG. 2E. The investment material 48 is then heated to remove the wax model 44. The investment material 48 is filled with a liquid metal (not shown), such as, for example, gold or another suitable material. Once the metal hardens, the investment cast 48 is broken to release a metal coping 46, which is shown in FIG. 2F. Typically, a porcelain cover 50 is attached to the metal coping 46 using well known techniques. The combination of the metal coping 46 and the porcelain cover 50 forms a final restoration 52.

The die spacer 40 ensures that the metal coping 46 has an internal cavity 54 that is slightly larger than the upper region 32 of the final abutment 10. Accordingly, as shown in FIG. 2F, there is a gap 56 between the final restoration 52 and the final abutment 10. This gap 56 provides room for the cement, which is used to secure the final restoration 52 to the final abutment 10.

It should be appreciated that any discontinuities 42 (see FIG. 2C) in the die spacer 40 are reproduced in the internal cavity 54 of the metal coping 46. Accordingly, the gap 56 typically has uneven portions 60 that have a thickness that is either larger or smaller than optimally desired. This can reduce the strength of the cement used to bond the final restoration 52 to the final abutment 10. The uneven portions 60 can also cause the final restoration 52 to sit too high or too low on the final abutment 30. Moreover, the uneven portions can cause the final restoration 52 to sit unevenly upon the final abutment 10. Accordingly, as shown in FIG. 2F, the final restoration 52 can undesirably tilt an angle β from the centerline of the final abutment 10 and the implant 12.

FIGS. 3A–3D illustrate a coping 100 having certain features and advantages according to the present invention. The illustrated coping 100 is configured to mate with the exemplary final abutment 10 and analogue 30 described above. Of course, those skilled in the art will recognize that the illustrated coping 100 can be modified to mate with abutments and analogues of different shapes and sizes.

The coping 100 comprises a main body 102. The main body 102 includes an inner surface 104 that defines an internal cavity 106. The inner surface 104 is configured such that the coping 100 can fit over the upper region 32 of the analogue 30 and the final abutment 10 described above. Accordingly, the coping 100 includes an anti-rotation member 108, which is configured to mate with the recess 36 of the analogue 30 and recess 20 of the final abutment 10 so as to prevent rotation of the coping 100 with respect to the analogue 30 and/or the final abutment 10.

The inner surface 104 also includes one or more feet or standoffs 110 and a top surface 115. Each standoff 110 preferably extends from the inner surface 104 towards the center of the cavity at least about 10 microns and often approximately 25 to 50 microns. However, it should be appreciated that the standoffs 110 can be configured to extend from the inner surface 104 more or less depending upon the desired thickness of the cement. Importantly, the standoffs 110 are small enough that they will not displace enough cement to weaken the bond between the final abutment 10 and the final restoration.

The inner surface 104 also preferably includes a flanged portion 112. The flanged portion 112 is configured to rest upon a lower portion or shoulder 114 of the analogue 30 (see FIG. 4A) and the final abutment 10 (see FIG. 1A). Preferably, the flanged portion 112 is sized and configured such that the coping 100 is centered on the analogue 30 and the top surface 115 of the inner surface 104 lies a desired distance (at least about 10 microns and often approximately 25–50 microns) above the final abutment 10.

The coping 100 and the standoffs 110 can be made using injection molding techniques. In other arrangements, the standoffs 110 can be formed by machining. In still other arrangements, the standoffs 110 can be separate pieces that are attached with, by way of example, an adhesive to the inner surface 104 of the coping.

Figure 4:
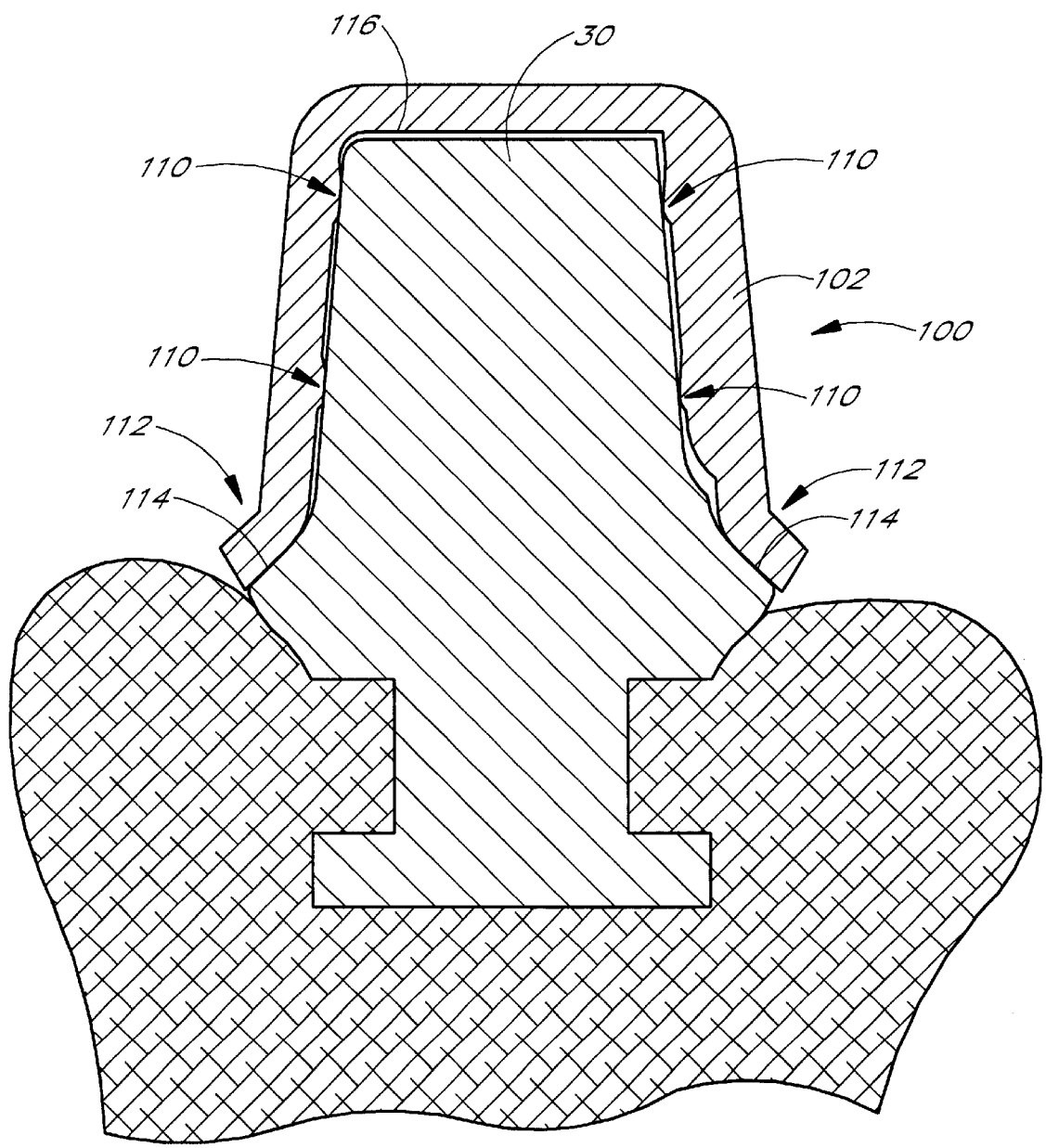
FIG. 4 is a cross-sectional side view of the coping of FIGS. 3A–D placed over the analogue of FIG. 2B embedded in a plaster model.

As shown in FIG. 4, when the coping 100 rests upon the analogue 30 the standoffs 110 and the flanged portion 112 cooperate to produce a uniform gap 116 between the coping 110 and the analogue 30. The thickness of the gap 116 is determined primarily by the distance the standoffs 110 extend from the inner surface 104 and the distance between the flanged portion 112 and the top surface 115. In some arrangements, the coping 100 may be formed without the standoffs 110 and in other arrangements without the flanged portion 112. In such arrangements, the standoffs 110 or the flanged portion 112 can be configured to produce a uniform 116 alone without the other feature. However, the illustrated arrangement is preferred because it provides a more stable coping 100 as compared to the other arrangements.

Figure 5A:
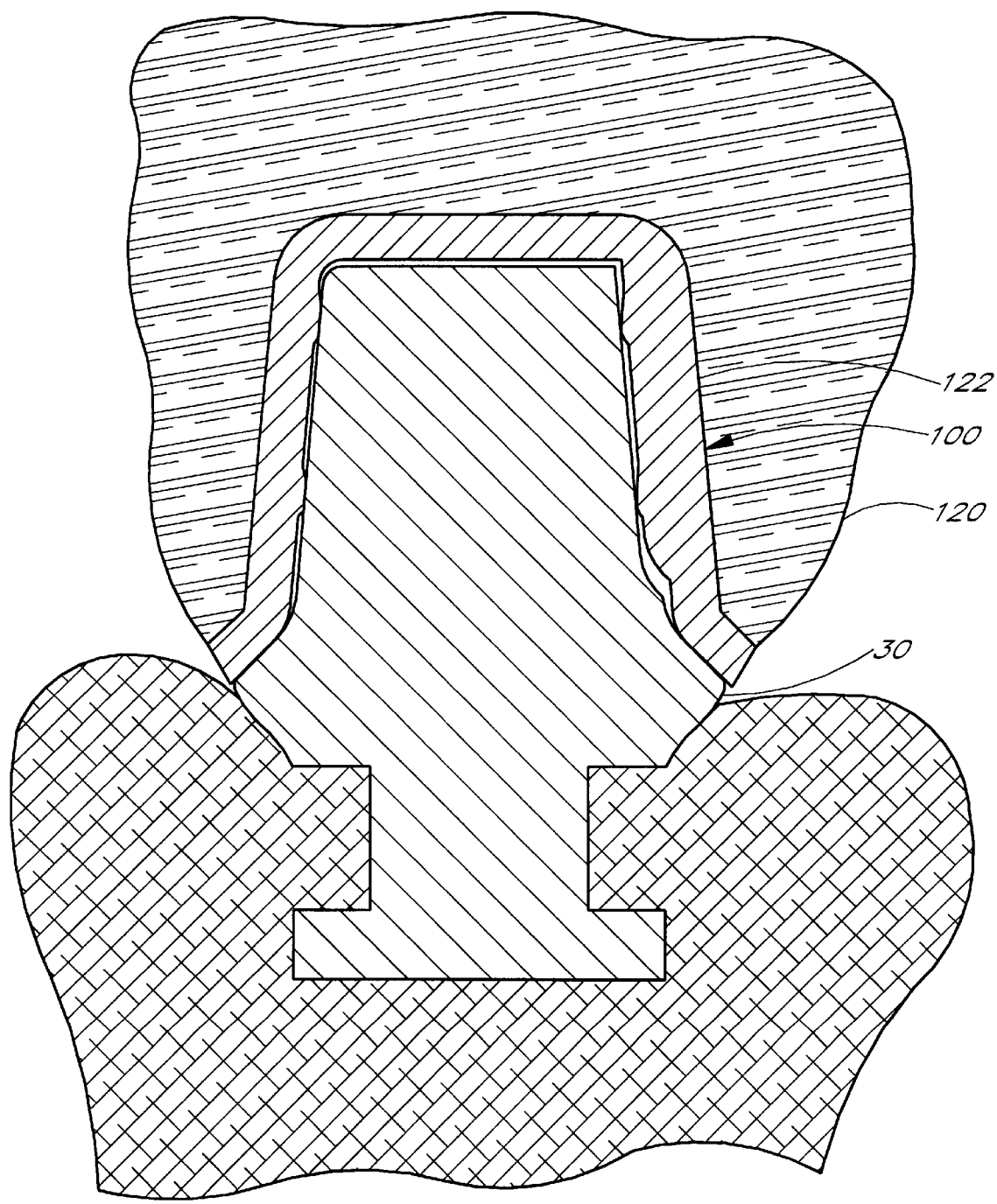
FIG. 5A is the coping of FIG. 4 covered with a wax model of a metal coping.
Figure 5B:
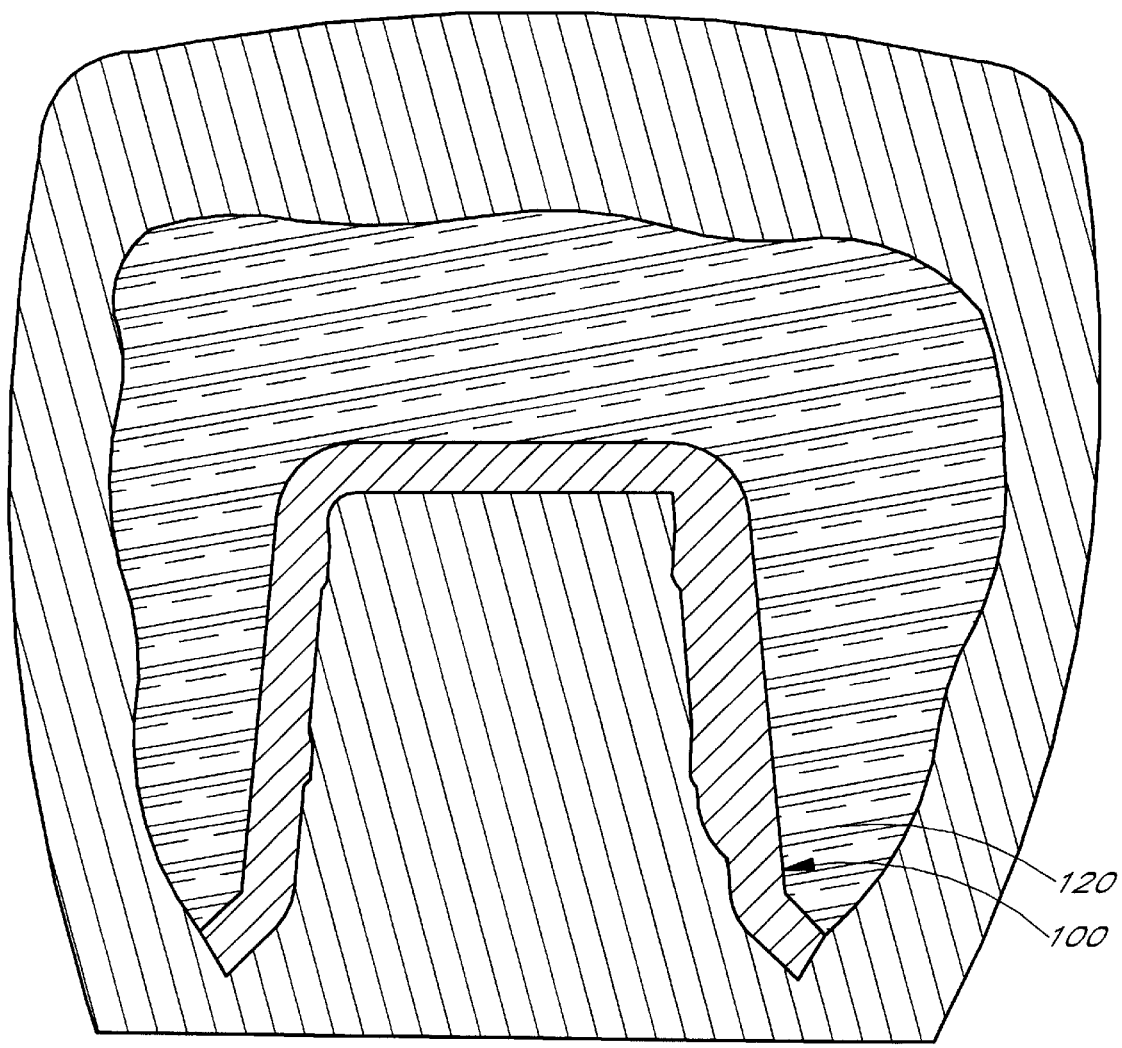
FIG. 5B is a cross-sectional view an investment casting of the coping and the wax model of FIG. 5A.

Several methods for creating a final restoration from the coping 100 will now be described. The first method utilizes investment casting techniques to create a metal coping with an inner surface substantially similar to the inner surface 104 of the coping 100. In this method, the coping 100 is made of plastic or another material suitable for investment casting. As shown in FIG. 5A, the technician applies, by way of example, wax 120 to the outer surface 122 of the coping 100 to form a model of a metal coping. The technician removes the wax 120 and the coping 100 from the analogue 30 and encases the combination in an investment material 124 (see FIG. 5B). The investment material 124 is then heated to remove the wax 120 and coping 100. The technician fills the investment material 124 with a metal, such as, for example, gold or another suitable material. Once the metal solidifies, the investment material 124 is broken to release the metal coping 130 (see FIG. 5C).

Figure 5C:
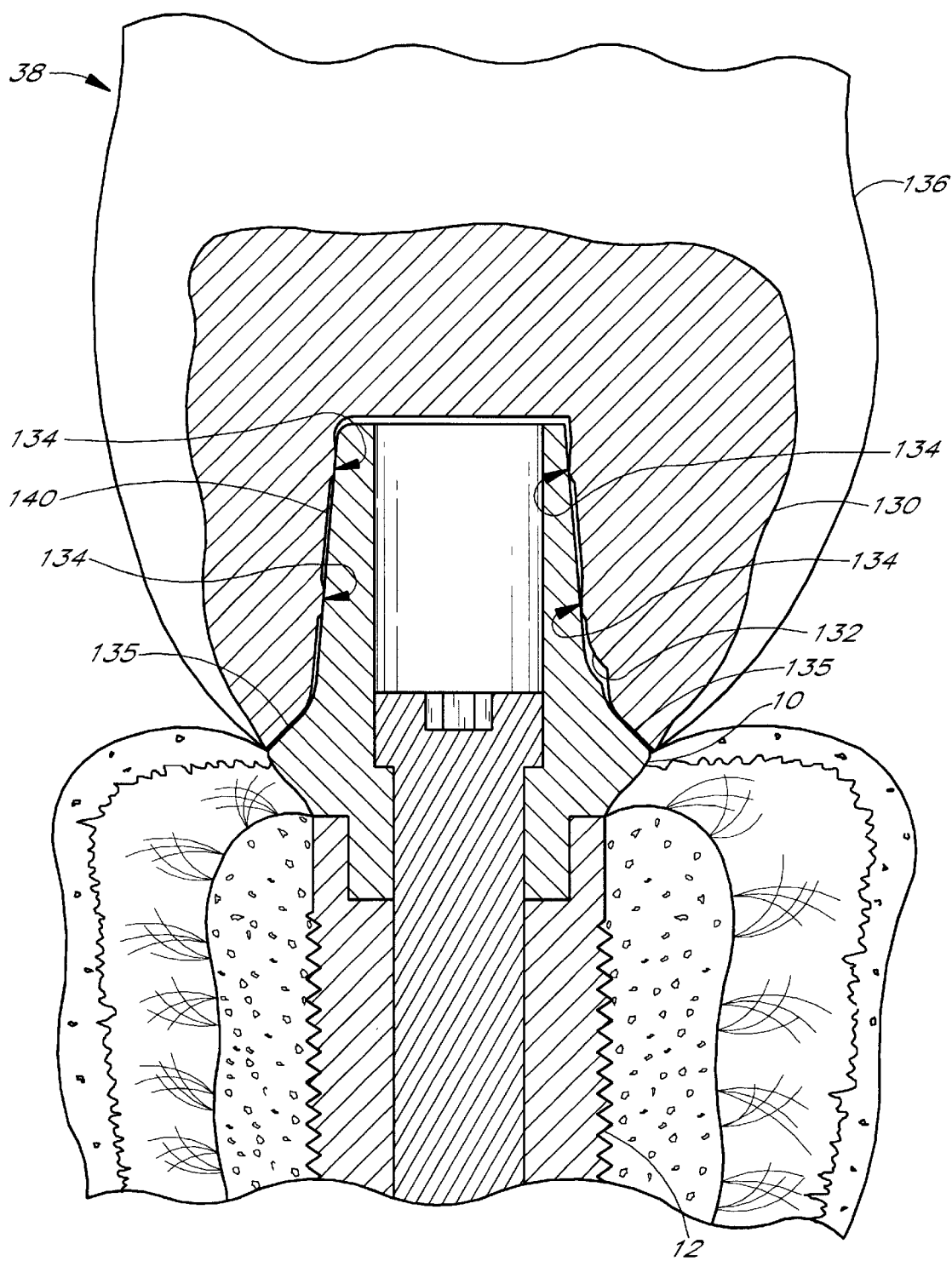
FIG. 5C is a cross-sectional side view of a metal coping and final restoration having certain features and advantages according to the present invention.

As shown in FIG. 5C, the metal coping 130 has an inner surface 132 that has substantially the same shape and size as the inner surface 104 of the plastic coping 100. Accordingly, the metal coping 130 includes standoffs 134 that are substantially the same size as the standoffs 110 of the plastic coping 100. Moreover, the inner surface 132 includes a top surface 133 and a lower flange 135 that are the same distance from each other as the top surface 115 and lower flange 112 of the plastic coping 100.

To form the final restoration 138, a porcelain cover 136 or other suitable tooth-like material is attached to the metal coping 130 using well known techniques. The metal coping 130 provides structural strength and rigidity to the final restoration 138.

With continued reference to FIG. 5C, when the final restoration 138 is placed upon the final abutment 10, the standoffs 134 and the lower flange 135 create a uniform gap 140 for the cement between the metal coping 130 and the final abutment 10. Moreover, the standoffs 134 help to center the final restoration 138 on the final abutment 10. Accordingly, the final restoration 138 rests squarely and evenly upon the final abutment 10.

With reference back to FIGS. 3A, 3C and 3D, the standoffs 134 preferably have a tapered shape. In other words, the standoffs 134 preferably have a inclined surface 141 (see FIG. 3D) that inclines radially outwardly (i.e., towards the center of the coping 100) in the direction of the opening of the internal cavity 106. In the illustrated arrangement, the inclined surfaces inclines at an angle of approximately three to five degrees with respect to the inner surface 104. The standoffs 134 preferably also have a cross-sectional width that increases in the direction of the opening of the internal cavity as best seen in FIG. 3A and FIG. 3C. The tapered shape of the standoffs 134 is preferred because it facilitates the standoffs ability to push aside any cement at the point of contact between the standoffs 134 and the final abutment 10. Accordingly, as shown in FIG. 5C, the standoffs 134 are in mating contact with the abutment 10. This also increases the stability of the final restoration 138. In other arrangements, the standoffs 134 can also have a cross-sectional width that decreases in the axial direction. In still other arrangements, the standoffs 134 can be formed without the tapered shape.

Figure 6:
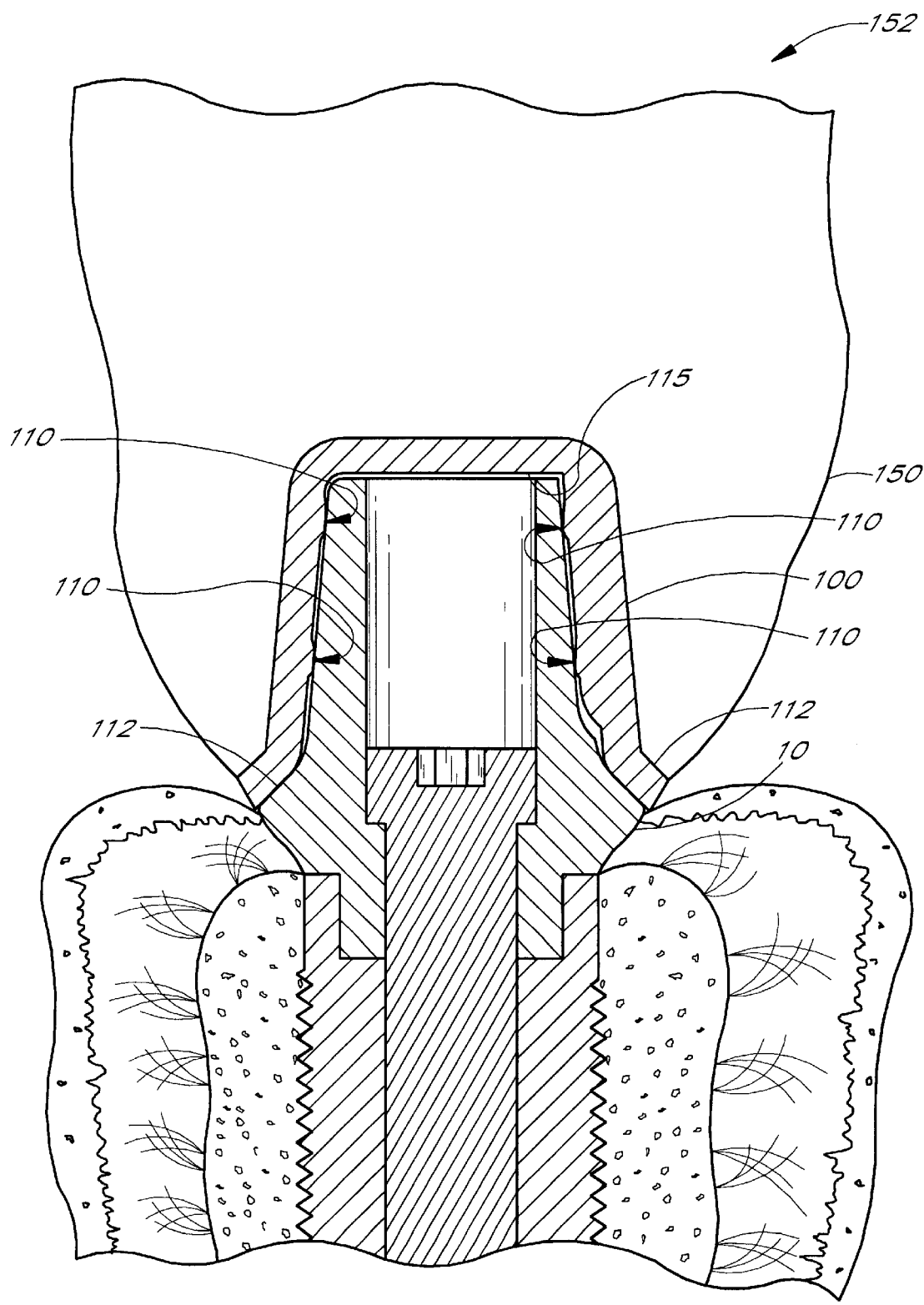
FIG. 6 is cross-sectional side view of another arrangement of a coping and final restoration having certain features and advantages according to the present invention.

A modified arrangement for creating a final restoration is illustrated in FIG. 6. In this arrangement, the coping 100 is made of material suitable for forming part of a final restoration, such as, for example, gold or a ceramic material. Preferably, the material is a ceramic fusing metal material to which, by way of example, porcelain can be directly fused. The coping 100 has substantially the same shape and size as the plastic coping described above. Accordingly, the coping 100 includes an inner surface 104 with a top surface 115, a flange 112 and a plurality standoffs 110. Because the coping 100 is made of a fairly rugged material, the coping 100 can form part of the final restoration 152. That is, a cover 150 made of porcelain or other suitable material can be directly attached to the coping 100, thereby forming the final restoration 152.

Figure 7A:
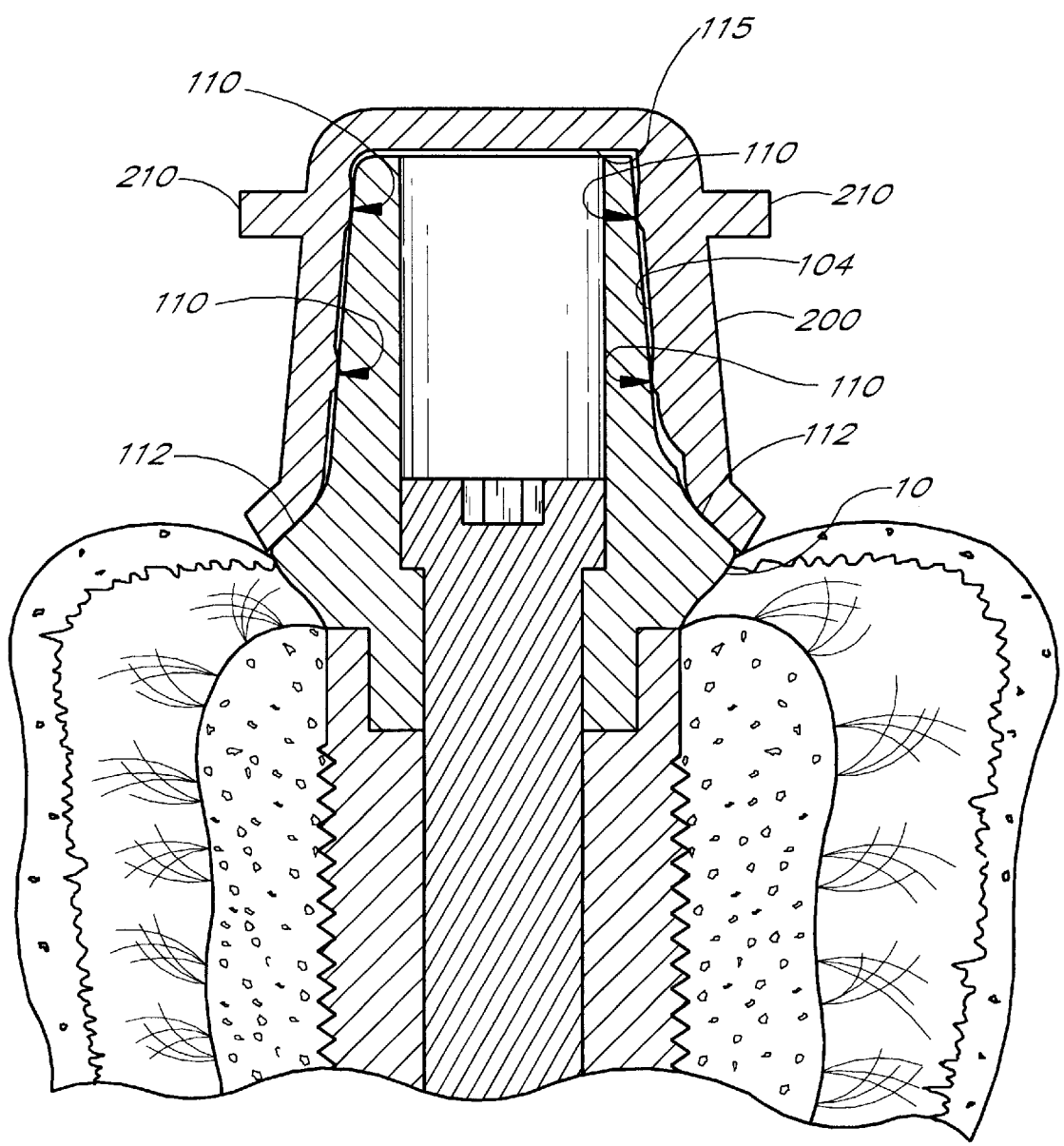
FIG. 7A is a cross-sectional side view of another arrangement of a coping having certain features and advantages according to the present invention.
Figure 7B:
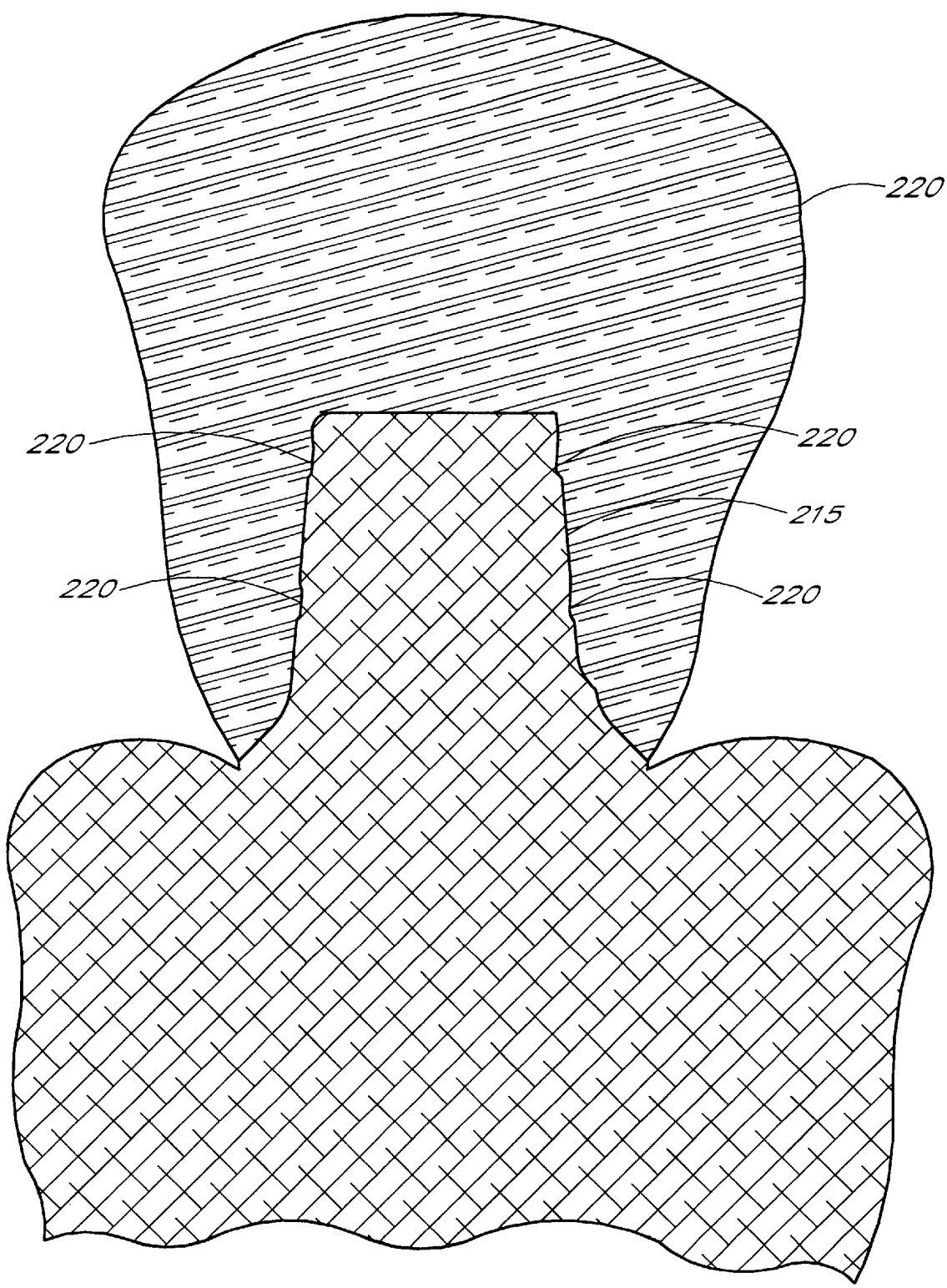
FIG. 7B is cross-sectional side view of a model of a final abutment having certain features and advantages according to the present invention.

Another modified arrangement for creating a final restoration is illustrated in FIGS. 7A–C. In this arrangement, the coping 200 is arranged substantially as described with respect to FIGS. 3A–3D. As such, the transfer coping 200 includes standoffs 110 and a flanged portion 112 that are substantially the same as the previous arrangements. Accordingly, there is a substantially uniform gap between the transfer coping 200 and the final abutment 10.

During, for example, stage II surgery, the surgeon can place the transfer coping 200 over the final abutment 10. The surgeon then places impression material (not shown) around the transfer coping 200 to record the position and orientation of the final abutment 10 in the patient's mouth. When the impression material is removed, the transfer coping 200 remains embedded in the impression material. In some arrangements, the coping 200 can include retention flanges (not shown) to facilitate holding the transfer coping 200 in the impression material.

A technician pours plaster into the impression to create a stone plaster model 215 of the patient's mouth and the final abutment 10. As shown in FIG. 6B, the stone plaster model 215 replicates the shape of the patient's mouth and the final abutment 10. However, the model 215 of the final abutment 10 is slightly larger than the final abutment 10 and includes indentations 220 that correspond to the standoffs 110 of the transfer coping 200. The technician applies wax 220 to the model 215 as in the previous arrangements to create a mold (not shown) for a metal coping. The metal coping formed from the wax 220 will have an inner surface that is substantially identical to the inner surface 104 of the transfer coping 200. Accordingly, the metal coping has an inner surface with standoffs 104 and a flange 112 that will produce a uniform gap between the final restoration and the final abutment as with the previous arrangements.

It should be appreciated that in some modified arrangements, the final abutment and/or analogue can be formed with feet or standoffs configured in a manner as described above. In such arrangements, the feet or standoffs extend away from the outer surface of the upper region and are thus positioned-between the outer surface of the final abutment and/or analogue and the inner surface of the final restoration so as to provide a gap as described above. In other arrangements, the final abutment, analogue and the coping can each be formed with feet or standoffs that are configured to cooperate to provide the gap.

FIGS. 8A–8D illustrate a modified final abutment 500, which includes certain features and advantages according to the present invention. The illustrated final abutment 500 includes an upper region 501 and an anti-rotation device 502. The anti-rotation device includes a substantially cylindrical portion 505 and protrusions 504, which are configured to fit within corresponding channels (not shown) formed in a dental implant (not shown). Accordingly, in the preferred arrangement, the protrusions 504 are arranged around the perimeter of the cylindrical portion 505 at approximately 120 degrees. Below the cylindrical portion 505 is a post 508. The post 508 is preferably substantially cylindrical and is configured to fit within a post-receiving chamber of the implant (not shown). The anti-rotation device 502 of this arrangement and of the corresponding dental implant are described in more detail in co-pending U.S. patent application Ser. No. 09/670,708 filed Sep. 17, 2000, which is hereby incorporated by reference herein.

The upper region 501 of the illustrated arrangement includes three grooves or recesses 510, which help to orient and prevent the rotation of a corresponding final restoration, which, as will be explained below, has an inner surface that generally corresponds to the shape of the upper region 501. It should be appreciated that in modified arrangements the upper region 501 can include more or less grooves or recesses 510.

The final abutment 500 also includes an inner bore 512 that is configured to receive a coupling screw (not shown), which is used to secure the final abutment 500 to the dental implant. Of course, as mentioned above, in modified arrangements the final abutment 500 can be formed without the inner bore 512.

FIGS. 9A–9D illustrate an analogue 550 for the final abutment 500 described above with respect to FIGS. 8A–8D. The analogue 550 includes an upper region 552 that has substantially the same shape and size as the upper region 501 of the final abutment 500. Accordingly, the upper region 552 of the illustrated analogue 550 also includes at least one grooves or recesses 554. The analogue 550 also includes a lower region 560, which is configured, as explained above with reference to FIGS. 2A and 2B, to be retained within, by way of example, a stone plaster model of the patient's mouth.

Figure 10A:
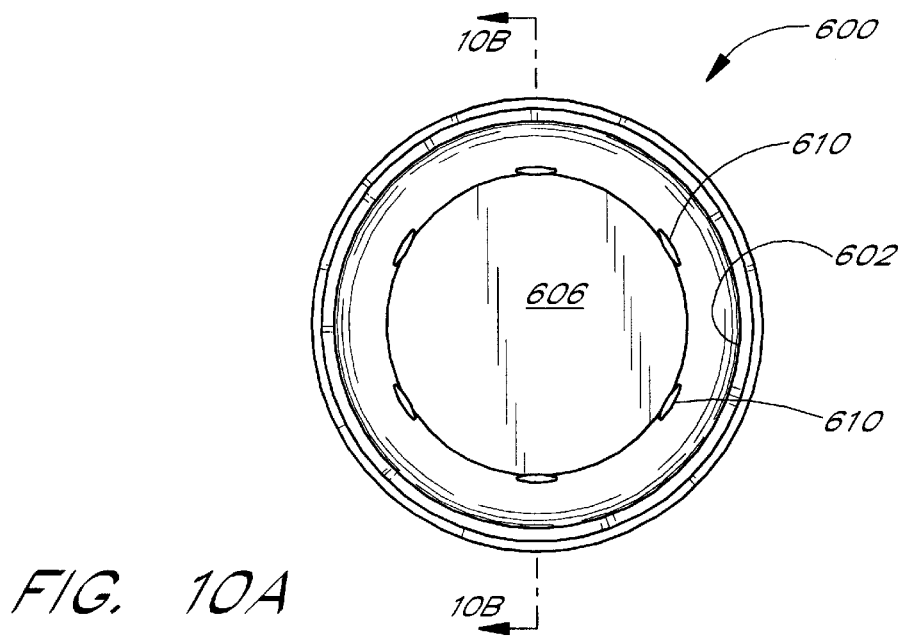
FIG. 10A is a bottom plan view of a modified coping having certain features and advantages according to the present invention.
Figure 10B:
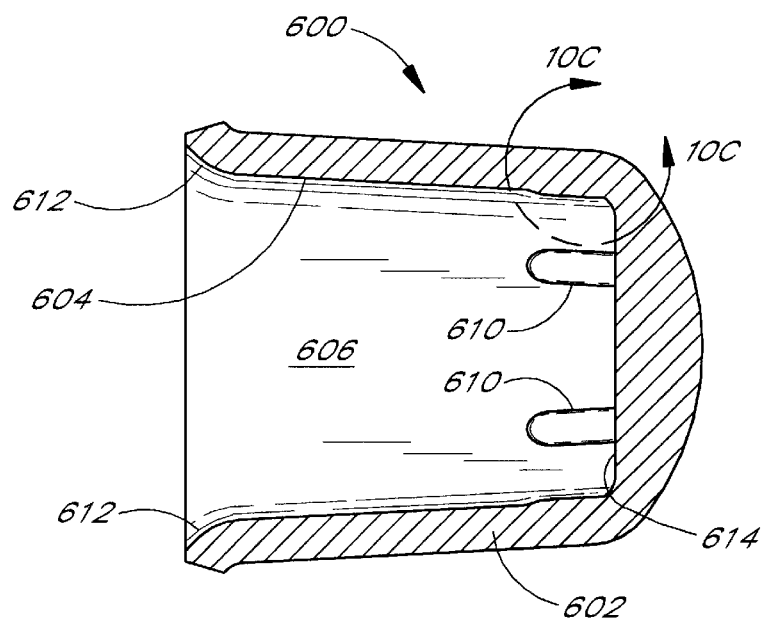
FIG. 10B is a cross-sectional view taken along line B—B of FIG. 10A.
Figure 10C:
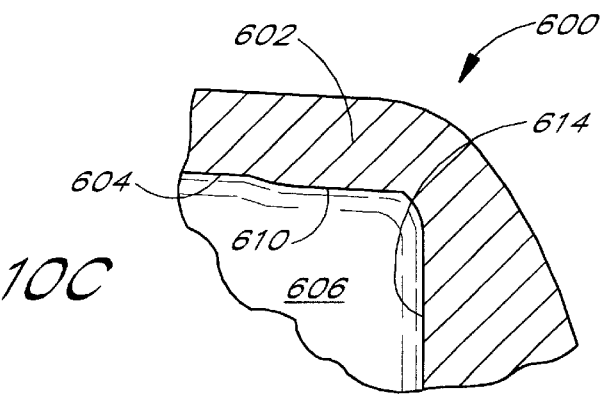
FIG. 10C is a close-up view of detail C of FIG. 10B.

FIGS. 10A–10C illustrate a coping 600 having certain features and advantages according to the present invention. The illustrated coping 600 is configured to mate with the final abutment 500 and analogue 550. The illustrated coping 600 has several features in common with the coping 100 described with reference to FIGS. 3A–3D. As such, the illustrated coping 600 can be used and formed in a manner as described above with particular reference to FIGS. 4–7B.

The illustrated coping 600 comprises a main body 602. The main body 602 includes an inner surface 604, that defines an internal cavity 606. The inner surface 604 is configured such that the coping 600 can fit over the upper region of the analogue 550 and the final abutment 500 described above.

The inner surface includes one or more feet or standoffs 610. As with the previous arrangements, each standoff 100 preferably extends from the inner surface 604 towards the center of the cavity 606 at least about 10 microns and often approximately 25–50 microns. The inner surface 604 preferably also includes a flanged portion 612, which is configured to rest upon a lower portion or shoulder 614 of the analogue 550 (see FIG. 9B) and the final abutment 500 (see FIG. 8B). Preferably, the flanged portion 612 is sized and configured such that the coping 600 is centered on the analogue and a top surface 615 of the inner surface 604 lies a desired distance (e.g., at least about 10 microns and often approximately 25–50 microns) above the final abutment 500.

Figure 11:
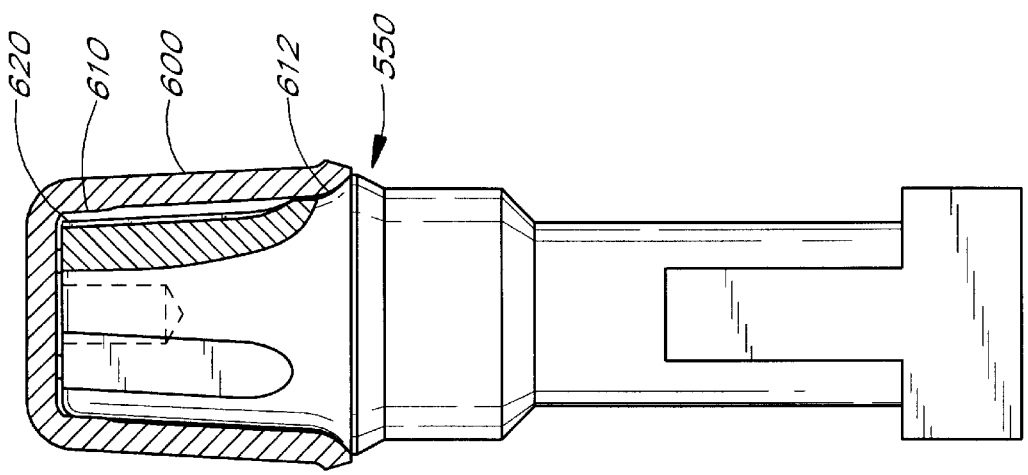
FIG. 11 is a cross-sectional side view of the coping of FIGS. 10A–C placed over the analogue of FIGS. 9A–D.

In the illustrated arrangement, the standoffs 610 preferably extend from the top surface 615 of the inner surface 604. Moreover, the coping 600 preferably includes six standoffs 610, which are preferably arranged around the perimeter of the inner surface 604 at approximately 60 degrees from each other. This arrangement is preferred because for any angular orientation of the illustrated coping 600 with respect to the final abutment 500 or analogue 550 at least one of the standoffs 610 do not lie within the recesses or grooves 512, 554 of the final abutment or analogue 550. As such, at least one standoff 610 contacts the outer surface of the final abutment 500 or analogue 550. In this manner, as shown in FIG. 11, the standoffs 610 and the flanged portion 612 cooperate to produce a substantially uniform gap 620 between the coping 600 and the analogue 550 or final abutment 500.

FIGS. 12A–12C illustrate another arrangement of a coping 700 having certain features and advantages according to the present invention. The illustrated coping 700 is also configured to mate with the final abutment 500 and analogue 550. As with the arrangement described above, the illustrated coping 700 has several features in common with the coping 100 described with reference to FIGS. 3A–3D. As such, the illustrated coping 700 can be used and formed in a manner as described above with particular reference to FIGS. 4–7B.

The illustrated coping 700 comprises a main body 702. The main body 702 includes an inner surface 704 that defines an internal cavity 706. The inner surface 704 is configured such that the coping 700 can fit over the upper region of the analogue 550 and the final abutment 500 described above.

The inner surface 704 includes one or more feet or standoffs 710. In this arrangement, the standoffs 710 are configured to fit within the grooves or recesses 510, 554 of the final abutment 500 (see FIGS. 8A–8D) and/or analogue 550 (see FIGS. 9A–9D). As such, the standoffs 710 help to orient and prevent the rotation of the coping 700 with respect to the final abutment 500 or analogue 550. The standoffs 710 are also configured such that the inner surface 704 of the coping lies at least about 10 microns and often approximately 25–50 microns above the outer surface of the final abutment or analogue 550. That is, the standoffs 710 are configured to extend from the inner surface 604 at least and additional 10 microns and often approximately 25–50 microns beyond the depth of the grooves or recesses 510, 554.

Figure 13:
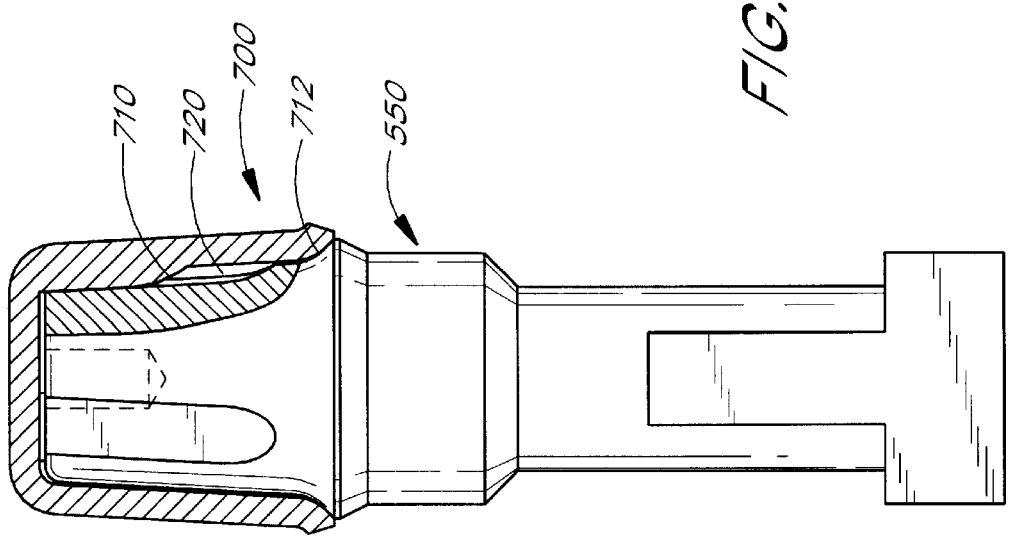
FIG. 13 is a cross-sectional side view of the coping of FIGS. 12A–C placed over the analogue of FIGS. 9A–D.

As with the previous, the inner surface 704 preferably also includes a flanged portion 712, which is configured to rest upon a lower portion or shoulder 614 of the analogue 550 (see FIG. 9B) and the final abutment 500 (see FIG. 8B). Preferably, the flanged portion 712 is sized and configured such that the coping 700 is centered on the analogue and a top surface 715 of the inner surface 704 lies a desired distance (e.g., at least about 10 microns and often approximately 25–50 microns) above the final abutment 600. In this manner, as shown in FIG. 13. the standoffs 710 and the flanged portion 712 cooperate to produce a uniform gap 720 between the coping 700 and the analogue 550 or final abutment 500.

It should be noted that for purposes of summarizing the invention and the advantages achieved over the prior art, certain objects and advantages of the invention have been described above herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

I claim:

1. A prosthodontic assembly comprising:
   a restoration having a cavity defined by a first surface;
   an abutment positioned within the cavity; and
   a plurality of standoffs positioned in between the first surface and the abutment to provide a gap.

2. A prosthodontic assembly as in claim 1, wherein at least some of the standoffs are on the abutment.

3. A prosthodontic assembly as in claim 1, wherein at least some of the standoffs are on the first surface.

4. A prosthodontic assembly as in claim 1, wherein the gap is at least 10 microns thick.

5. A prosthodontic assembly as in claim 1, wherein the gap is between approximately 25 microns and 50 microns thick.

6. A prosthodontic assembly as in claim 1, wherein the plurality of standoffs have a tapered shape.

7. A prosthodontic assembly as in claim 6, wherein the first surface is made of gold.

8. A prosthodontic assembly as in claim 6, wherein the first surface is made of a ceramic material.

9. A prosthodontic assembly as in claim 1, wherein the final restoration includes a flanged region that is configured to rest upon a shoulder of the abutment.

10. A prosthodontic assembly comprising:
    a first prosthodontic component comprising an upper region with at least one recess, and
    a coping configured for creating a final restoration, the coping comprising a body portion having a proximal end, a distal end and an inner surface that defines an internal cavity and at least one standoff that extends from the inner surface towards a center of the internal cavity, the at least one standoff being configured to fit within the at least one recesses so as to prevent relative rotation between the first prosthodontic component and the coping, the at least one standoff also being configured to provide a gap between the inner surface of the coping and the upper region of the first prosthodontic component.

11. A prosthodontic assembly as in claim 10, wherein the first prosthodontic is a final abutment.

12. A prosthodontic assembly as in claim 10, wherein the first prosthodontic is an analogue of a final abutment.

13. A prosthodontic assembly as in claim 10, wherein the gap is at least 10 microns thick.

14. A prosthodontic assembly as in claim 13, wherein the gap is between approximately 25 microns and 50 microns thick.

15. A prosthodontic assembly as in claim 10, wherein the coping is made of a material that can be melted and removed from a mold during an investment casting process.

16. A prosthodontic assembly as in claim 15, wherein the coping is made of plastic.

17. A prosthodontic assembly as in claim 10, wherein the coping is made from a material that is suitable for forming a portion of the final restoration.

18. A prosthodontic assembly as in claim 17, wherein the coping is made of gold.

19. A prosthodontic assembly as in claim 17, wherein the coping is made of a ceramic material.

20. A prosthodontic assembly as in claim 10, wherein the at least one of standoff has a tapered shape.

21. A prosthodontic assembly as in claim 10, wherein the coping includes a flanged region that is configured to rest upon a shoulder of the first prosthodontic component.

22. A prosthodontic assembly comprising:
    a coping having a cavity defined by a first surface;
    an abutment positioned within the cavity; and
    a plurality of standoffs positioned in between the first surface and the coping to provide a gap.

23. A prosthodontic assembly as in claim 22, wherein the gap is at least 10 microns thick.

24. A prosthodontic assembly as in claim 22, wherein the gap is between approximately 25 microns and 50 microns thick.

25. A prosthodontic assembly as in claim 22, wherein the coping is made of a material that can be melted and removed from a mold during an investment casting process.

26. A prosthodontic assembly as in claim 25, wherein the coping is made of plastic.

27. A prosthodontic assembly as in claim 22, wherein the coping is made from a material that is suitable for forming a portion of the final restoration.

28. A prosthodontic assembly as in claim 27, wherein the coping is made of gold.

29. A prosthodontic assembly as in claim 27, wherein the coping is made of a ceramic material.

30. A prosthodontic assembly as in claim 22, wherein the plurality of standoffs have a tapered shape.

31. A prosthodontic assembly as in claim 22, wherein the coping includes a flanged region that configured to rest upon a shoulder of the abutment.

32. A prosthodontic assembly comprising:
    a final restoration comprising a body portion having a proximal end, a distal end and an inner surface that defines an internal cavity, the inner surface including a top region and a flanged region, and at least one standoff that extends from the inner surface towards a center of the internal cavity; and
    an abutment positioned within the cavity;
    wherein the at least one standoff and the flanged region are configured to produce a substantially uniform gap between the final restoration and the abutment upon which the final restoration rests.

33. A prosthodontic assembly as in claim 32, wherein the gap is at least 10 microns thick.

34. A prosthodontic assembly as in claim 32, wherein the gap is between approximately 25 microns and 50 microns thick.

35. A prosthodontic assembly as in claim 32, wherein the at least one standoff is made of gold.

36. A prosthodontic assembly as in claim 32, wherein the at least one standoff is made of a ceramic material.

37. A prosthodontic assembly as in claim 32, wherein the at least one standoff has a tapered shape.

38. A prosthodontic assembly comprising:
    a coping comprising a body portion having a proximal end, a distal end and an inner surface that defines an internal cavity, the inner surface including a top region, a flanged region, at least one standoff that extends from the inner surface towards a center of the internal cavity; and
    an abutment positioned within the internal cavity;
    wherein the at least one standoff and the flanged region are configured to produce a substantially uniform gap between the coping and the abutment upon which the coping rests.

39. A prosthodontic assembly as in claim 38, wherein the gap is at least 10 microns thick.

40. A prosthodontic assembly as in claim 38, wherein the gap is between approximately 25 microns and 50 microns thick.

41. A prosthodontic assembly as in claim 38, wherein the coping is made of a material that can be melted and removed from a mold during an investment casting process.

42. A prosthodontic assembly as in claim 41, wherein the coping is made of plastic.

43. A prosthodontic assembly as in claim 38, wherein the coping is made from a material that is suitable for forming a portion of the final restoration.

44. A prosthodontic assembly as in claim 43, wherein the coping is made of gold.

45. A prosthodontic assembly as in claim 43, wherein the coping is made of a ceramic material.

46. A prosthodontic assembly as in claim 38, wherein the at least one of standoff has a tapered shape.

* * * * *